(12) United States Patent
Maimon et al.

(10) Patent No.: US 10,856,971 B2
(45) Date of Patent: Dec. 8, 2020

(54) SEALING MEMBERS FOR PROSTHETIC HEART VALVE

(71) Applicant: Edwards Lifesciences Corporation, Irvine, CA (US)

(72) Inventors: David Maimon, Haifa (IL); Tamir S. Levi, Zikhron Yaakov (IL)

(73) Assignee: Edwards Lifesciences Corporation, Irvine, CA (US)

( * ) Notice: Subject to any disclaimer, the term of this patent is extended or adjusted under 35 U.S.C. 154(b) by 149 days.

(21) Appl. No.: 16/103,973

(22) Filed: Aug. 16, 2018

(65) Prior Publication Data

US 2019/0053898 A1 Feb. 21, 2019

Related U.S. Application Data

(60) Provisional application No. 62/547,322, filed on Aug. 18, 2017.

(51) Int. Cl.
*A61F 2/24* (2006.01)
(52) U.S. Cl.
CPC .......... *A61F 2/2418* (2013.01); *A61F 2/2409* (2013.01); *A61F 2/2433* (2013.01); *A61F 2/2436* (2013.01); *A61F 2220/0016* (2013.01); *A61F 2220/0075* (2013.01); *A61F 2230/001* (2013.01); *A61F 2230/0019* (2013.01); *A61F 2230/0054* (2013.01); *A61F 2250/0039* (2013.01); *A61F 2250/0063* (2013.01); *A61F 2250/0069* (2013.01)

(58) Field of Classification Search
CPC ...... A61F 2/24–2496; A61F 2230/0019; A61F 2/07–2002/077
See application file for complete search history.

(56) References Cited

U.S. PATENT DOCUMENTS

| 9,668,857 | B2 * | 6/2017 | Braido | A61F 2/2418 |
|---|---|---|---|---|
| 9,687,341 | B2 | 6/2017 | Alkhatib et al. | |
| 9,820,852 | B2 * | 11/2017 | Braido | A61F 2/2403 |
| 9,913,715 | B2 * | 3/2018 | Braido | A61F 2/2418 |
| 9,949,825 | B2 * | 4/2018 | Braido | A61F 2/2412 |
| 10,130,467 | B2 * | 11/2018 | Braido | A61F 2/2418 |
| 10,258,464 | B2 * | 4/2019 | Delaloye | A61F 2/2409 |
| 10,321,993 | B2 * | 6/2019 | Li | A61F 2/2418 |
| 2006/0122686 | A1 * | 6/2006 | Gilad | A61F 2/2418 |
| | | | | 623/1.13 |

(Continued)

FOREIGN PATENT DOCUMENTS

WO 2010008548 A2 1/2010
WO 2014110171 A2 7/2014

*Primary Examiner* — Tan-Uyen T Ho
*Assistant Examiner* — Charles M Wei
(74) *Attorney, Agent, or Firm* — Klarquist Sparkman, LLC; Hans P. Smith

(57) ABSTRACT

An implantable prosthetic valve can include a radially expandable and collapsible annular frame comprising an inflow end and an outflow end. The frame can have a plurality of struts forming a plurality of cells, wherein each of the plurality of cells defines an opening in the frame. A leaflet structure can be positioned within the frame and secured thereto. A plurality of sealing members can be positioned within the openings of a plurality of the cells of the frame and secured thereto. Each of the plurality of sealing members can be positioned within a respective one of the openings.

20 Claims, 14 Drawing Sheets

(56) References Cited

U.S. PATENT DOCUMENTS

| | | | |
|---|---|---|---|
| 2006/0122693 A1* | 6/2006 | Biadillah | A61F 2/2418 |
| | | | 623/1.24 |
| 2013/0018458 A1 | 1/2013 | Yohanan et al. | |
| 2013/0274873 A1* | 10/2013 | Delaloye | A61F 2/2409 |
| | | | 623/2.18 |
| 2014/0277417 A1 | 9/2014 | Schraut et al. | |
| 2015/0127098 A1* | 5/2015 | Braido | A61F 2/2418 |
| | | | 623/2.17 |
| 2015/0209136 A1* | 7/2015 | Braido | A61F 2/2403 |
| | | | 623/2.18 |
| 2016/0250022 A1* | 9/2016 | Braido | A61F 2/2418 |
| | | | 623/2.38 |
| 2016/0361160 A1* | 12/2016 | Braido | A61F 2/2412 |
| 2017/0079786 A1* | 3/2017 | Li | A61F 2/2418 |
| 2017/0086971 A1* | 3/2017 | Braido | A61F 2/2418 |
| 2017/0165053 A1* | 6/2017 | Buesseler | A61F 2/2412 |
| 2017/0312398 A1* | 11/2017 | Ulmer | A61L 31/16 |
| 2017/0354765 A1* | 12/2017 | Ulmer | A61L 29/043 |

* cited by examiner

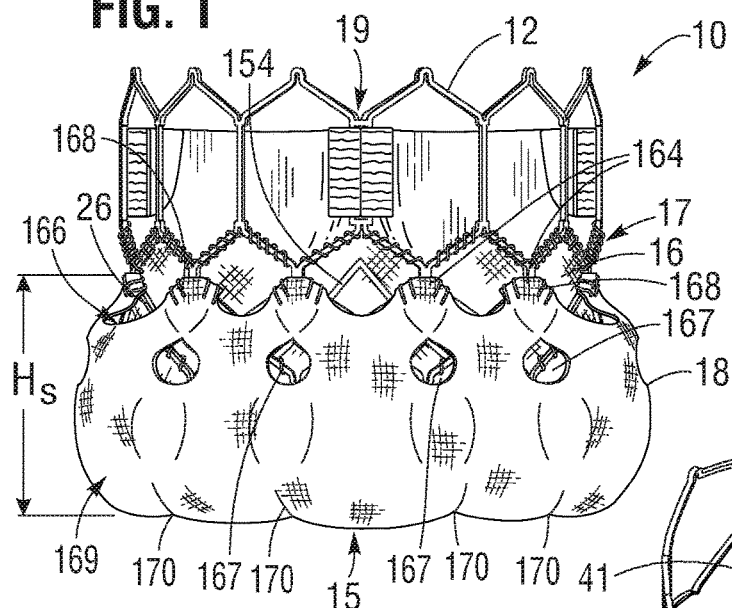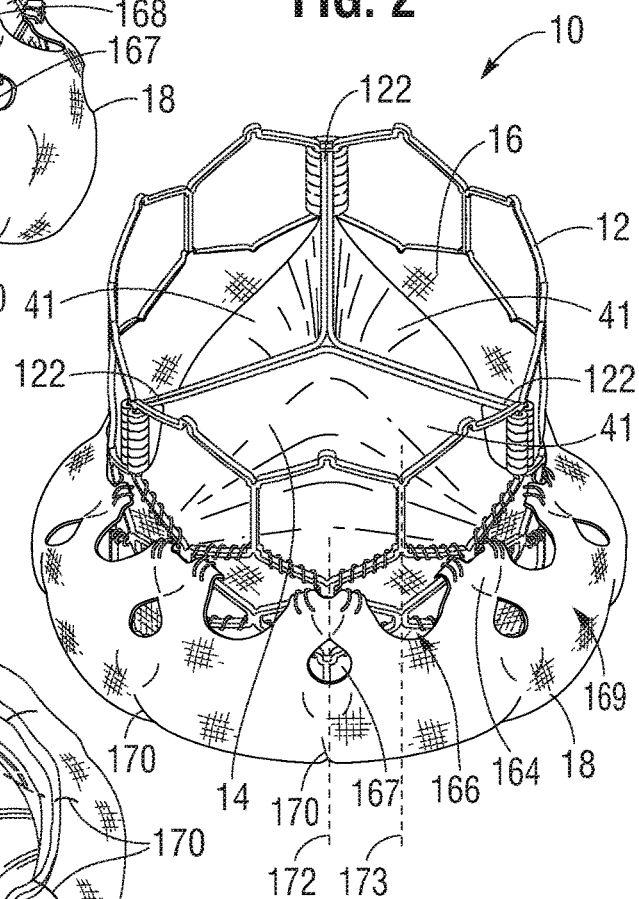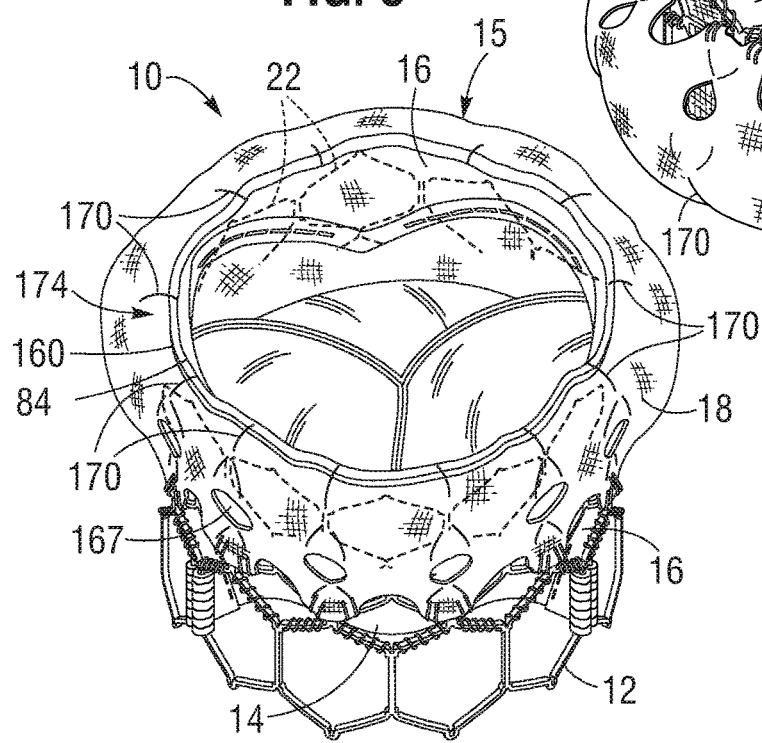

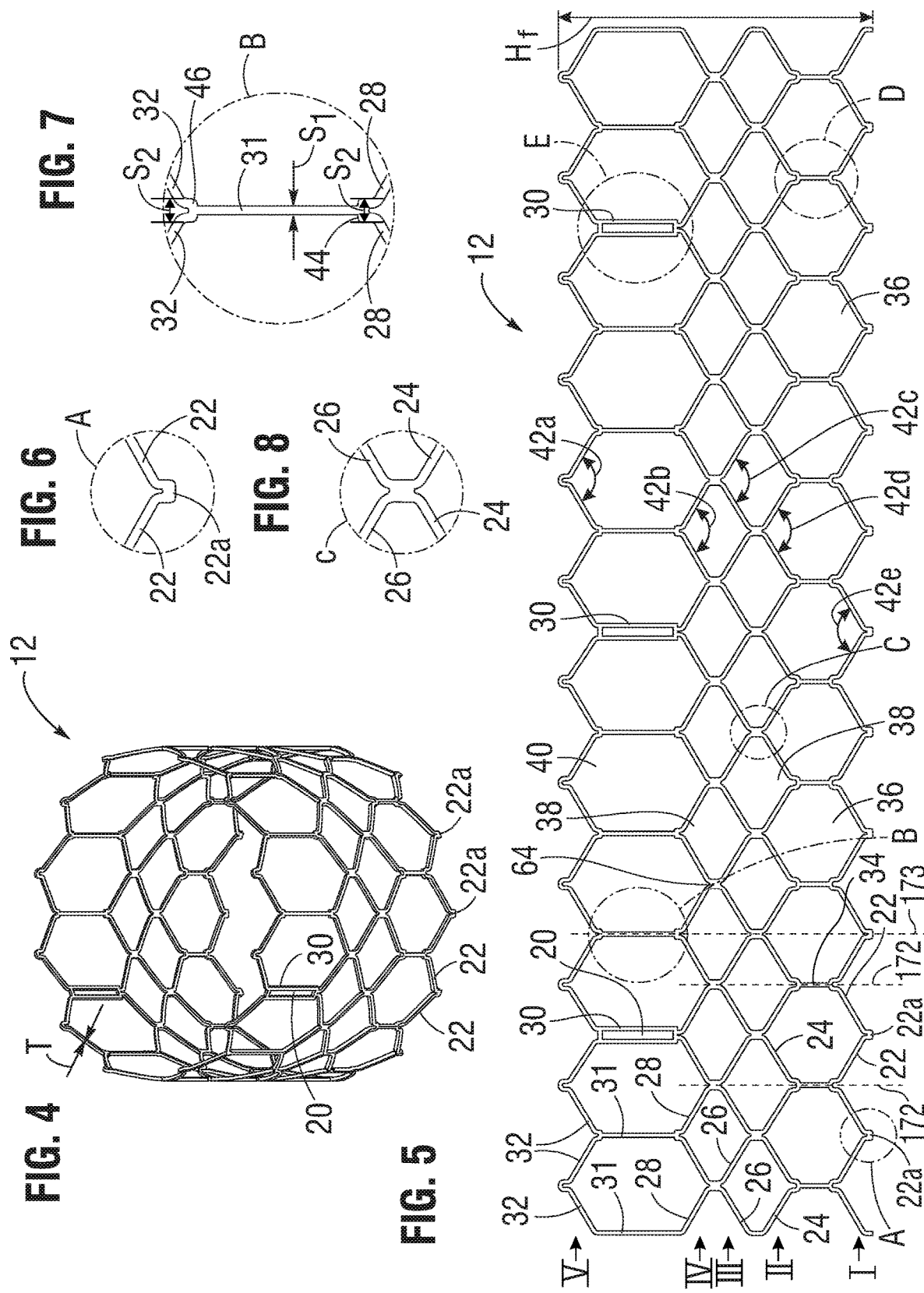

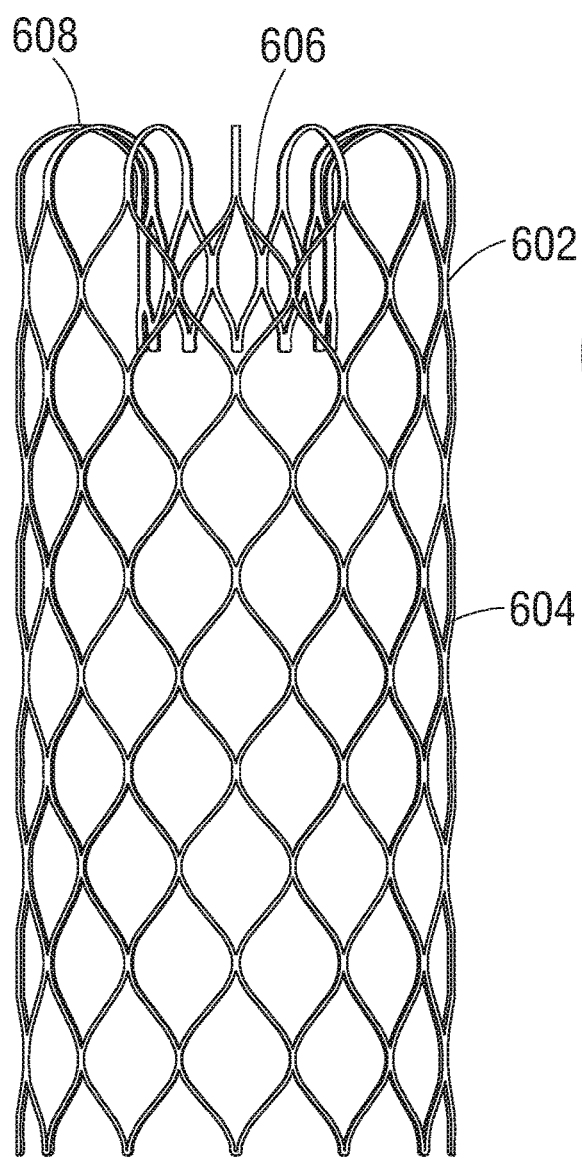
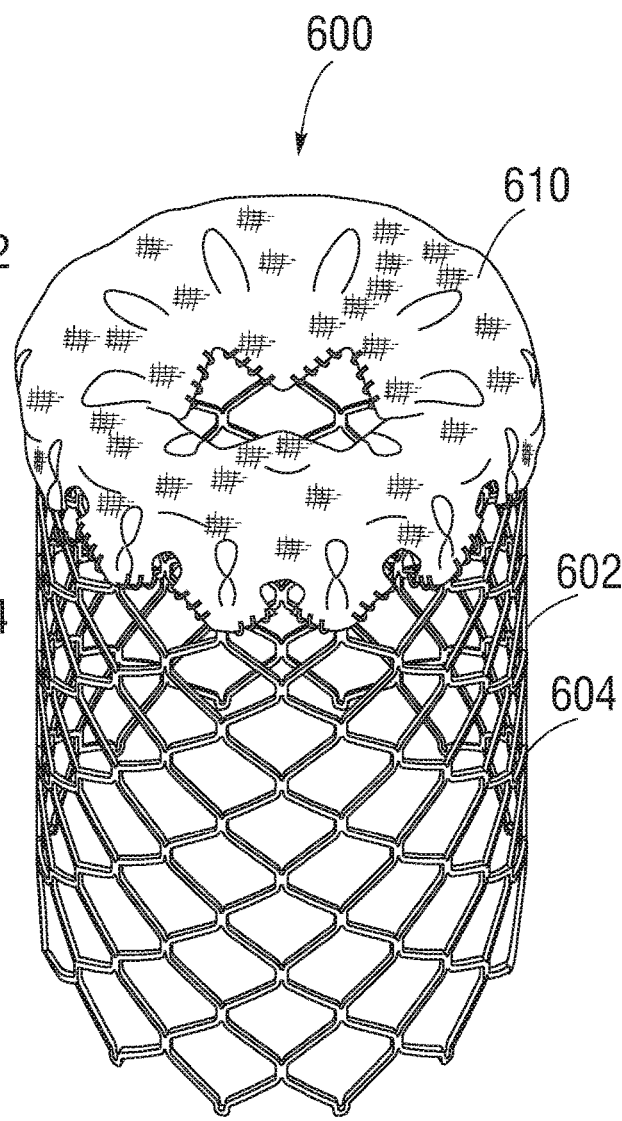
FIG. 29
FIG. 30

SEALING MEMBERS FOR PROSTHETIC HEART VALVE

CROSS REFERENCE TO RELATED APPLICATION

This application claims the benefit of U.S. Provisional Application Ser. No. 62/547,322, filed Aug. 18, 2017, which is incorporated by reference herein.

FIELD

The present disclosure relates to implantable, expandable prosthetic devices and to methods and apparatuses for such prosthetic devices.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans. Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For example, collapsible transcatheter prosthetic heart valves can be crimped to a compressed state and percutaneously introduced in the compressed state on a catheter and expanded to a functional size at the desired position by balloon inflation or by utilization of a self-expanding frame or stent.

A prosthetic valve for use in such a procedure can include a radially collapsible and expandable frame to which leaflets of the prosthetic valve can be coupled. For example, U.S. Pat. Nos. 6,730,118, 7,393,360, 7,510,575, and 7,993,394, which are incorporated herein by reference in their entirety, describe exemplary collapsible and expandable transcatheter prosthetic heart valves.

A prosthetic valve for use in such a procedure can include a radially collapsible and expandable frame to which leaflets of the prosthetic valve can be coupled, and which can be percutaneously introduced in a collapsed configuration on a catheter and expanded in the desired position by balloon inflation or by utilization of a self-expanding frame or stent. A challenge in catheter-implanted prosthetic valves is control of perivalvular leakage around the valve, which can occur for a period of time following initial implantation. An additional challenge includes the process of crimping such a prosthetic valve to a profile suitable for percutaneous delivery to a subject.

SUMMARY

Embodiments of a radially collapsible and expandable prosthetic valve are disclosed herein that include improved outer sealing members for reducing perivalvular leakage, as well as related methods and apparatuses including such prosthetic valves. In several embodiments, the disclosed prosthetic valves are configured as replacement heart valves for implantation into a subject.

In one representative embodiment, an implantable prosthetic heart valve can comprise an annular frame, a leaflet structure positioned within the frame and secured thereto, and a plurality of sealing members. The annular frame can comprise an inflow end, an outflow end, and a plurality of struts forming a plurality of cells. Each of the cells can define an opening in the frame and the frame can be radially collapsible and expandable between a radially collapsed configuration and a radially expanded configuration. The sealing members can be positioned within the openings of a plurality of the cells of the frame and secured thereto. Each of the sealing members can be positioned within a respective one of the openings.

In some embodiments, the sealing members can be substantially rectangular and two opposite sides of each of the sealing members can be secured to the frame and the other two opposite sides of each of the sealing members can be not secured to the frame.

In some embodiments, the sealing members can be substantially rectangular and two opposite sides of each of the sealing members can be secured to struts of the frame and the other two opposite sides of each of the sealing members can be not secured to the frame.

In some embodiments, the frame can comprise multiple rows of cells. In such embodiments, one of the sealing members can be secured within each cell of the row of cells closest to the inflow end of the frame.

In some embodiments, the frame can comprise multiple rows of cells. In such embodiments, one of the sealing members can be secured within each cell of the two rows of cells closest to the inflow end of the frame.

In some embodiments, each of the sealing members can have the same orientation with respect to the frame.

In some embodiments, a first set of the sealing members can each have a first orientation with respect to the frame and the remainder of the sealing members not in the first set can each have a second orientation with respect to the frame that is different from the first orientation.

In some embodiments, the first orientation can be a clockwise orientation and the second orientation can be a counter-clockwise orientation.

In some embodiments, the sealing members in one of the two rows of cells closest to the inflow end of the frame can each have a first orientation with respect to the frame and the sealing members in the other of the first two rows of cells closest to the inflow end of the frame can each have a second orientation different from the first orientation.

In some embodiments, the sealing members can be secured to the frame with sutures.

In some embodiments, the prosthetic valve can further comprise an annular inner skirt arranged around an inner surface of the frame and secured thereto.

In some embodiments, the sealing members can be loosely secured to the frame such that the sealing members positioned within the cells of the frame comprise excess material to expand away from the frame when blood flows along an outer surface of the frame.

In some embodiments, the sealing members can be positioned such that when the prosthetic valve is implanted, antegrade blood can flow between the frame and the plurality of sealing members.

In another representative embodiment, an assembly for implanting a prosthetic heart valve can comprise a delivery apparatus a delivery apparatus comprising an elongate shaft and a prosthetic heart valve that can be coupled to the shaft of the delivery apparatus. The prosthetic heart valve can comprise an annular frame, a leaflet structure positioned within the frame and secured thereto, and a plurality of sealing members. The annular frame can comprise an inflow end, an outflow end, and a plurality of struts forming a plurality of cells. Each of the cells can define an opening in the frame. The frame can be radially collapsible and expandable between a radially collapsed configuration and a radially expanded configuration. The sealing members can be positioned within the openings of a plurality of the cells of the frame and secured thereto. Each of the sealing members can be positioned within a respective one of the openings.

In some embodiments, each of the sealing members can have the same orientation with respect to the frame.

In some embodiments, a first set of the sealing members can each have a first orientation with respect to the frame and the remainder of the sealing members not in the first set can each have a second orientation different than the first orientation.

In another representative embodiment, a method of implanting a prosthetic heart valve can comprise radially compressing the heart valve to a radially compressed configuration, coupling the prosthetic heart valve to a distal end portion of a delivery apparatus, inserting the distal end portion of the delivery apparatus and the prosthetic heart valve into a patient's body, positioning the prosthetic heart valve adjacent a native valve of the patient's heart, and radially expanding the prosthetic heart valve so that it engages the native valve. The prosthetic heart valve can comprise an annular frame, a leaflet structure positioned within the frame and secured thereto, and a plurality of sealing members. The annular frame can comprise an inflow end, an outflow end, and a plurality of struts forming a plurality of cells. Each of the cells can define an opening in the frame. The frame can be radially collapsible and expandable between a radially collapsed configuration and a radially expanded configuration. The sealing members can be positioned within the openings of a plurality of the cells of the frame and secured thereto. Each of the sealing members can be positioned within a respective one of the openings.

In some embodiments, each of the sealing members can have the same orientation with respect to the frame.

In some embodiments, a first set of the sealing members can each have a first orientation with respect to the frame and the remainder of the sealing members not in the first set can each have a second orientation with respect to the frame that is different than the first orientation.

The foregoing and other objects, features, and advantages of the disclosure will become more apparent from the following detailed description, which proceeds with reference to the accompanying figures.

BRIEF DESCRIPTION OF THE DRAWINGS

FIGS. 1-3 show an exemplary embodiment of a prosthetic heart valve.

FIGS. 4-10 show an exemplary frame of the prosthetic heart valve of FIG. 1.

FIGS. 29-30 show an alternative embodiment of a docking device for a prosthetic valve.

DETAILED DESCRIPTION

Figure 9:
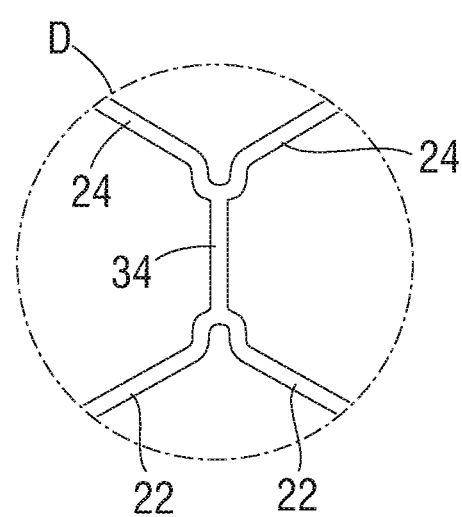
Figure 10:
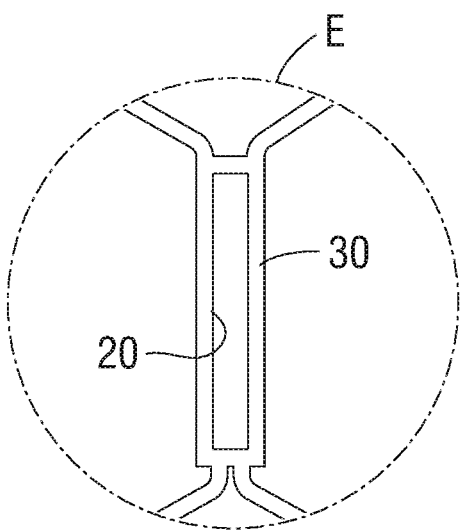
Figure 11:
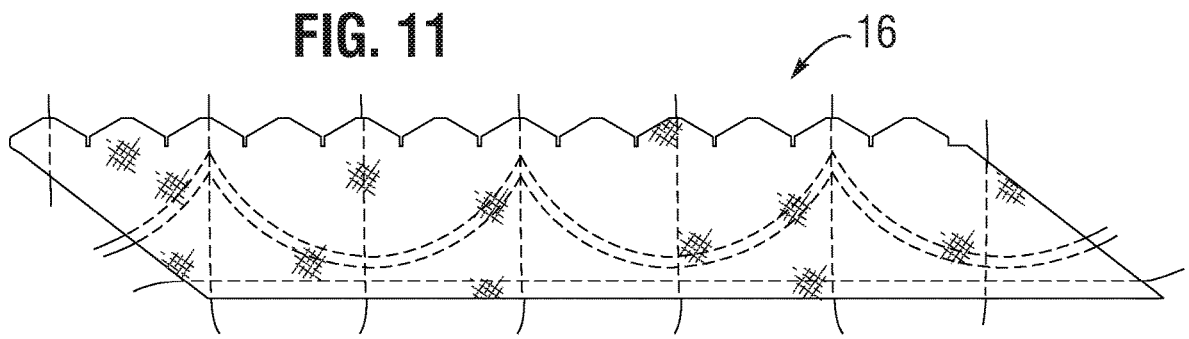
FIGS. 11-12 show an exemplary inner skirt of the prosthetic heart valve of FIG. 1.

FIGS. 1-3 show various views of a prosthetic heart valve 10, according to one embodiment. The illustrated prosthetic valve is adapted to be implanted in the native aortic annulus, although in other embodiments it can be adapted to be implanted in the other native annuluses of the heart (e.g., the pulmonary, mitral, and tricuspid valves). The prosthetic valve can also be adapted to be implanted in other tubular organs or passageways in the body. The prosthetic valve 10 can have four main components: a stent or frame 12, a valvular structure 14, an inner skirt 16, and a perivalvular sealing means or sealing member. The prosthetic valve 10 can have an inflow end portion 15, an intermediate portion 17, and an outflow end portion 19. In the illustrated embodiment, the perivalvular sealing means comprises an outer skirt 18.

The valvular structure 14 can comprise three leaflets 41, collectively forming a leaflet structure, which can be arranged to collapse in a tricuspid arrangement, as best shown in FIG. 2. The lower edge of leaflet structure 14 desirably has an undulating, curved scalloped shape (suture line 154 shown in FIG. 21 tracks the scalloped shape of the leaflet structure). By forming the leaflets with this scalloped geometry, stresses on the leaflets are reduced, which in turn improves durability of the prosthetic valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the prosthetic valve. The leaflets 41 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference in its entirety herein.

The bare frame 12 is shown in FIG. 4. The frame 12 can be formed with a plurality of circumferentially spaced slots, or commissure windows, 20 (three in the illustrated embodiment) that are adapted to connect the commissures of the valvular structure 14 to the frame, as described in greater detail below. The frame 12 can be made of any of various suitable plastically-expandable materials (e.g., stainless steel, etc.) or self-expanding materials (e.g., nickel titanium alloy (NiTi), such as nitinol). When constructed of a plastically-expandable material, the frame 12 (and thus the prosthetic valve 10) can be crimped to a radially collapsed configuration on a delivery catheter and then expanded inside a patient by an inflatable balloon or equivalent expansion mechanism. When constructed of a self-expandable material, the frame 12 (and thus the prosthetic valve 10) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size.

Suitable plastically-expandable materials that can be used to form the frame 12 include, without limitation, stainless steel, a biocompatible, high-strength alloys (e.g., a cobalt-chromium or a nickel-cobalt-chromium alloys), polymers, or combinations thereof. In particular embodiments, frame 12 is made of a nickel-cobalt-chromium-molybdenum alloy, such as MP35N® alloy (SPS Technologies, Jenkintown, Pa.), which is equivalent to UNS R30035 alloy (covered by ASTM F562-02). MP35N® alloy/UNS R30035 alloy comprises 35% nickel, 35% cobalt, 20% chromium, and 10% molybdenum, by weight. When MP35N® alloy is used as the frame material, as compared to stainless steel, less material is needed to achieve the same or better performance in radial and crush force resistance, fatigue resistances, and corrosion resistance. Moreover, since less material is required, the crimped profile of the frame can be reduced, thereby providing a lower profile prosthetic valve assembly for percutaneous delivery to the treatment location in the body.

Referring to FIGS. 4 and 5, the frame 12 in the illustrated embodiment comprises a first, lower row I of angled struts 22 arranged end-to-end and extending circumferentially at the inflow end of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end of the frame. A plurality of substantially straight axially extending struts 34 can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28. FIGS. 6, 7, 8, 9, and 10 are enlarged views of the portions of the frame 12 identified by letters A, B, C, D, and E, respectively, in FIG. 5.

Each commissure window frame portion 30 connects to a respective commissure of the leaflet structure 14. As can be seen each frame portion 30 is secured at its upper and lower ends to the adjacent rows of struts to provide a robust configuration that enhances fatigue resistance under cyclic loading of the prosthetic valve compared to cantilevered struts for supporting the commissures of the leaflet structure. This configuration enables a reduction in the frame wall thickness to achieve a smaller crimped diameter of the prosthetic valve. In particular embodiments, the thickness T of the frame 12 (FIG. 4) measured between the inner diameter and outer diameter is about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 40. The openings 40 are relatively large and are sized to allow portions of the leaflet structure 14 to protrude, or bulge, into and/or through the openings 40 when the frame 12 is crimped in order to minimize the crimping profile.

Figure 13:
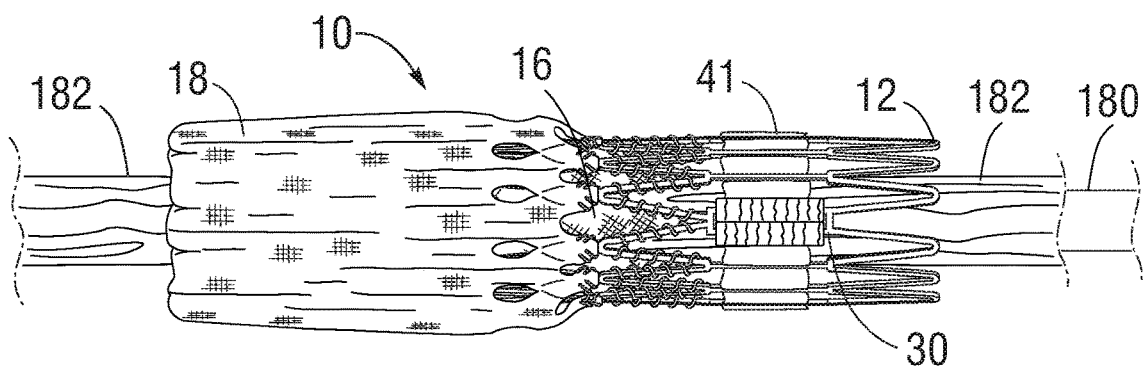
FIG. 13 shows the prosthetic heart valve of FIG. 1 in a collapsed configuration and mounted on an exemplary balloon catheter.

As best shown in FIG. 7, the lower end of the strut 31 is connected to two struts 28 at a node or junction 44, and the upper end of the strut 31 is connected to two struts 32 at a node or junction 46. The strut 31 can have a thickness 51 that is less than the thicknesses S2 of the junctions 44, 46. The junctions 44, 46, along with junctions 64, prevent full closure of openings 40. FIG. 13 shows the prosthetic valve 10 crimped on a balloon catheter. As can be seen, the geometry of the struts 31, and junctions 44, 46, and 64 assists in creating enough space in openings 40 in the collapsed configuration to allow portions of the prosthetic leaflets to protrude or bulge outwardly through openings. This allows the prosthetic valve to be crimped to a relatively smaller diameter than if all of the leaflet material were constrained within the crimped frame.

The frame 12 is configured to reduce, to prevent, or to minimize possible over-expansion of the prosthetic valve at a predetermined balloon pressure, especially at the outflow end portion of the frame, which supports the leaflet structure 14. In one aspect, the frame is configured to have relatively larger angles 42a, 42b, 42c, 42d, 42e between struts, as shown in FIG. 5. The larger the angle, the greater the force required to open (expand) the frame. As such, the angles between the struts of the frame can be selected to limit radial expansion of the frame at a given opening pressure (e.g., inflation pressure of the balloon). In particular embodiments, these angles are at least 110 degrees or greater when the frame is expanded to its functional size, and even more particularly these angles are up to about 120 degrees when the frame is expanded to its functional size.

In addition, the inflow and outflow ends of a frame generally tend to over-expand more so than the middle portion of the frame due to the "dog-boning" effect of the balloon used to expand the prosthetic valve. To protect against over-expansion of the leaflet structure 14, the leaflet structure desirably is secured to the frame 12 below the upper row of struts 32, as best shown in FIG. 1. Thus, in the event that the outflow end of the frame is over-expanded, the leaflet structure is positioned at a level below where over-expansion is likely to occur, thereby protecting the leaflet structure from over-expansion.

In one type of prosthetic valve construction, portions of the leaflets protrude longitudinally beyond the outflow end of the frame when the prosthetic valve is crimped if the leaflets are connected too close to the distal end of the frame. If the delivery catheter on which the crimped prosthetic valve is mounted includes a pushing mechanism or stop member that pushes against or abuts the outflow end of the prosthetic valve (for example, to maintain the position of the crimped prosthetic valve on the delivery catheter), the pushing member or stop member can damage the portions of the exposed leaflets that extend beyond the outflow end of the frame. Another benefit of connecting the leaflets at a location spaced away from the outflow end of the frame is that when the prosthetic valve is crimped on a delivery catheter, the outflow end of the frame 12 rather than the leaflets 41 is the proximal-most component of the prosthetic valve 10. As such, if the delivery catheter includes a pushing mechanism or stop member that pushes against or abuts the outflow end of the prosthetic valve, the pushing mechanism or stop member contacts the outflow end of the frame, and not leaflets 41, so as to avoid damage to the leaflets.

Also, as can be seen in FIG. 5, the openings 36 of the lowermost row of openings in the frame are relatively larger than the openings 38 of the two intermediate rows of openings. This allows the frame, when crimped, to assume an overall tapered shape that tapers from a maximum diameter at the outflow end of the prosthetic valve to a minimum diameter at the inflow end of the prosthetic valve. When crimped, the frame 12 can have a reduced diameter region extending along a portion of the frame adjacent the inflow end of the frame that generally corresponds to the region of the frame covered by the outer skirt 18. In some embodiments, the reduced diameter region is reduced compared to the diameter of the upper portion of the frame (which is not covered by the outer skirt) such that the outer skirt 18 does not increase the overall crimp profile of the prosthetic valve. When the prosthetic valve is deployed, the frame can expand to the generally cylindrical shape shown in FIG. 4. In one example, the frame of a 26-mm prosthetic valve, when crimped, had a first diameter of 14 French at the outflow end of the prosthetic valve and a second diameter of 12 French at the inflow end of the prosthetic valve.

The main functions of the inner skirt 16 are to assist in securing the valvular structure 14 to the frame 12 and to assist in forming a good seal between the prosthetic valve and the native annulus by blocking the flow of blood through the open cells of the frame 12 below the lower edge of the leaflets. The inner skirt 16 desirably comprises a tough, tear resistant material such as polyethylene terephthalate (PET), although various other synthetic materials or natural materials (e.g., pericardial tissue) can be used. The thickness of the skirt desirably is less than about 0.15 mm (about 6 mil), and desirably less than about 0.1 mm (about 4 mil), and even more desirably about 0.05 mm (about 2 mil). In particular embodiments, the skirt 16 can have a variable thickness, for example, the skirt can be thicker at least one of its edges than at its center. In one implementation, the skirt 16 can comprise a PET skirt having a thickness of about 0.07 mm at its edges and about 0.06 mm at its center. The thinner skirt can provide for better crimping performances while still providing good sealing.

Figure 20:
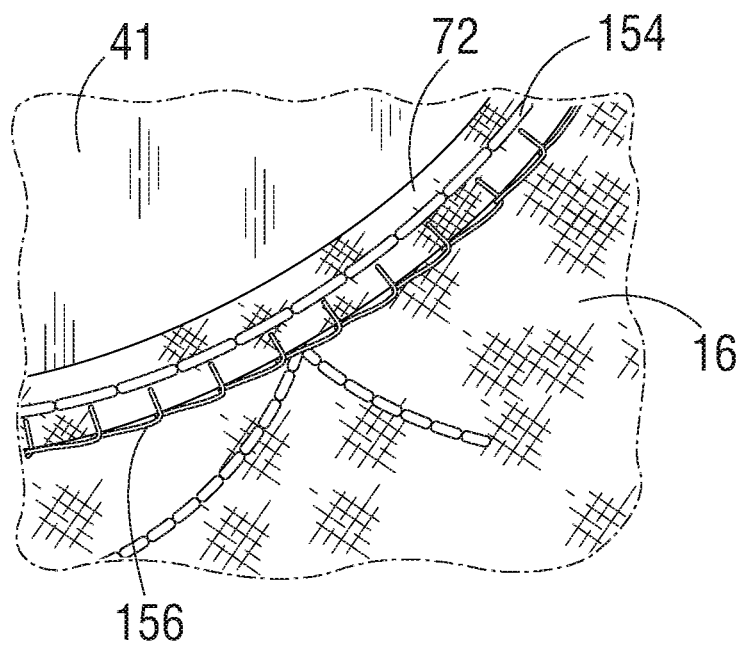
FIGS. 20-21 show the assembly of the leaflet structure with the inner skirt along a lower edge of the leaflets.
Figure 21:
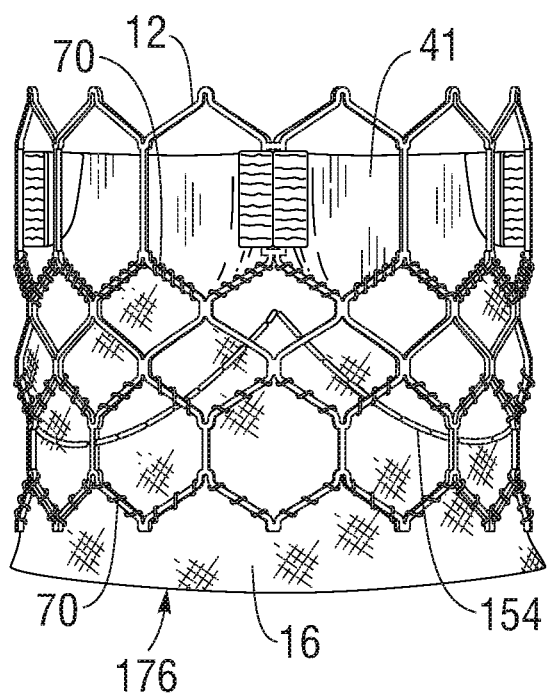

The skirt 16 can be secured to the inside of frame 12 via sutures 70, as shown in FIG. 21. Valvular structure 14 can be attached to the skirt via one or more reinforcing strips 72 (which collectively can form a sleeve), for example thin, PET reinforcing strips, discussed below, which enables a secure suturing and protects the pericardial tissue of the leaflet structure from tears. Valvular structure 14 can be sandwiched between skirt 16 and the thin PET strips 72 as shown in FIG. 20. Sutures 154, which secure the PET strip and the leaflet structure 14 to skirt 16, can be any suitable suture, such as Ethibond Excel® PET suture (Johnson & Johnson, New Brunswick, N.J.). Sutures 154 desirably track the curvature of the bottom edge of leaflet structure 14, as described in more detail below.

Some fabric skirts comprise a weave of warp and weft fibers that extend perpendicularly to each other and with one set of the fibers extending longitudinally between the upper and lower edges of the skirt. When the metal frame to which such a fabric skirt is secured is radially compressed, the overall axial length of the frame increases. However, a fabric skirt with limited elasticity cannot elongate along with the frame and therefore tends to deform the struts of the frame and to prevent uniform crimping.

Figure 12:
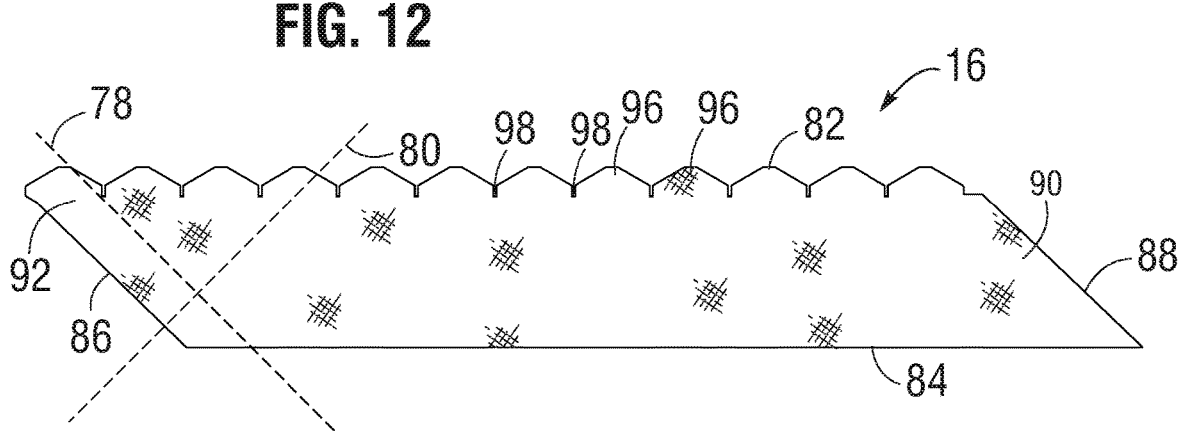

Referring to FIG. 12, in one embodiment, the skirt 16 desirably is woven from a first set of fibers, or yarns or strands, 78 and a second set of fibers, or yarns or strands, 80, both of which are non-perpendicular to the upper edge 82 and the lower edge 84 of the skirt. In particular embodiments, the first set of fibers 78 and the second set of fibers 80 extend at angles of about 45 degrees (e.g., 15-75 degrees or 30-60 degrees) relative to the upper and lower edges 82, 84. For example, the skirt 16 can be formed by weaving the fibers at 45 degree angles relative to the upper and lower edges of the fabric. Alternatively, the skirt 16 can be diagonally cut (cut on a bias) from a vertically woven fabric (where the fibers extend perpendicularly to the edges of the material) such that the fibers extend at 45 degree angles relative to the cut upper and lower edges of the skirt. As further shown in FIG. 12, the opposing short edges 86, 88 of the skirt desirably are non-perpendicular to the upper and lower edges 82, 84. For example, the short edges 86, 88 desirably extend at angles of about 45 degrees relative to the upper and lower edges and therefore are aligned with the first set of fibers 78. Therefore the overall general shape of the skirt can be that of a rhomboid or parallelogram.

Figure 14:
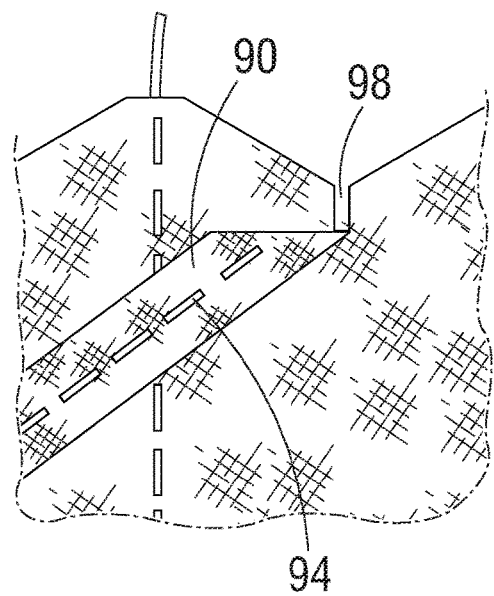
FIGS. 14-16 show the assembly of the inner skirt of FIG. 11 with the frame of FIG. 4.
Figure 15:
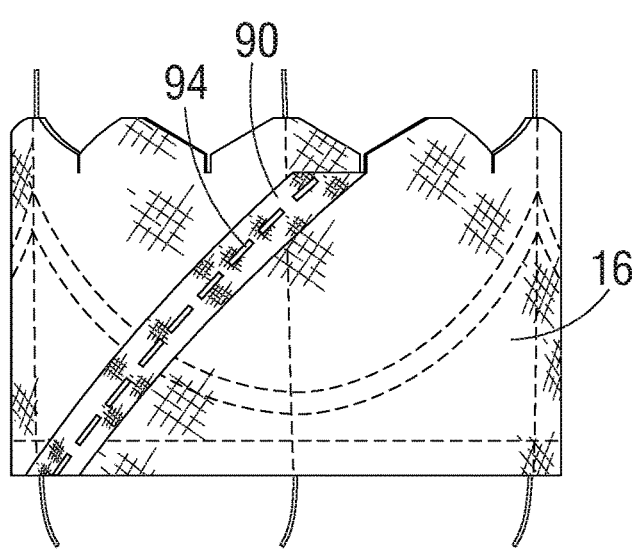
Figure 16:
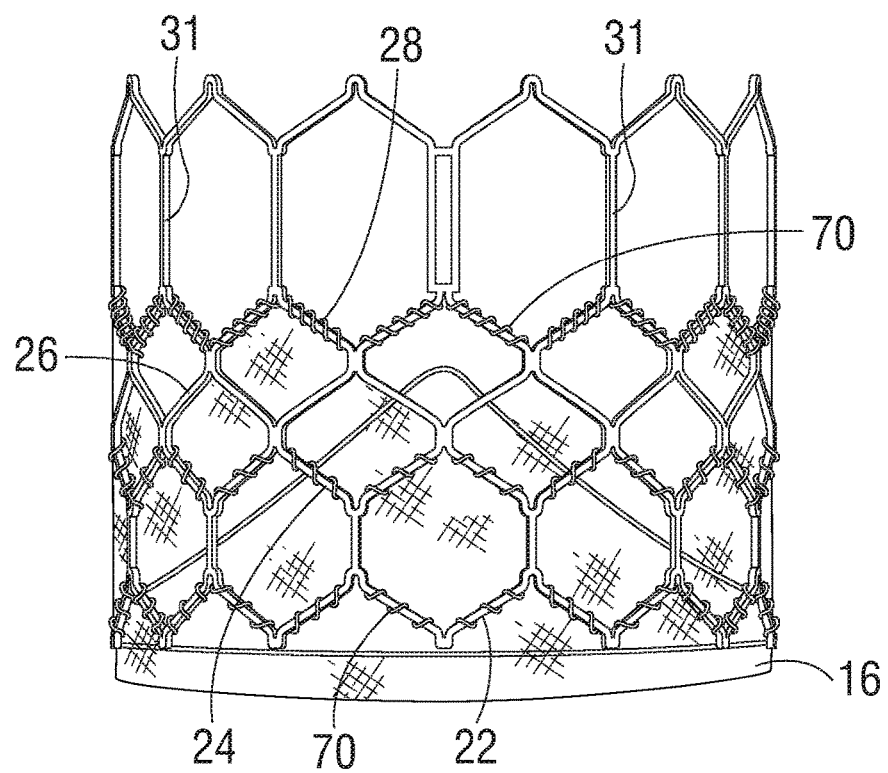

FIGS. 14 and 15 show the inner skirt 16 after opposing short edge portions 90, 92 have been sewn together to form the annular shape of the skirt. As shown, the edge portion 90 can be placed in an overlapping relationship relative to the opposite edge portion 92, and the two edge portions can be sewn together with a diagonally extending suture line 94 that is parallel to short edges 86, 88. The upper edge portion of the inner skirt 16 can be formed with a plurality of projections 96 that define an undulating shape that generally follows the shape or contour of the fourth row of struts 28 immediately adjacent the lower ends of axial struts 31. In this manner, as best shown in FIG. 16, the upper edge of the inner skirt 16 can be tightly secured to struts 28 with sutures 70. The inner skirt 16 can also be formed with slits 98 to facilitate attachment of the skirt to the frame. Slits 98 can be dimensioned so as to allow an upper edge portion of the inner skirt 16 to be partially wrapped around struts 28 and to reduce stresses in the skirt during the attachment procedure. For example, in the illustrated embodiment, the inner skirt 16 is placed on the inside of frame 12 and an upper edge portion of the skirt is wrapped around the upper surfaces of struts 28 and secured in place with sutures 70. Wrapping the upper edge portion of the inner skirt 16 around struts 28 in this manner provides for a stronger and more durable attachment of the skirt to the frame. The inner skirt 16 can also be secured to the first, second, and/or third rows of struts 22, 24, and 26, respectively, with sutures 70.

Referring again to FIG. 12, due to the angled orientation of the fibers relative to the upper and lower edges in this embodiment, the skirt can undergo greater elongation in the axial direction (i.e., in a direction from the upper edge 82 to the lower edge 84).

Thus, when the metal frame 12 is crimped (as shown in FIG. 13), the inner skirt 16 can elongate in the axial direction along with the frame and therefore provide a more uniform and predictable crimping profile. Each cell of the metal frame in the illustrated embodiment includes at least four angled struts that rotate towards the axial direction on crimping (e.g., the angled struts become more aligned with the length of the frame). The angled struts of each cell function as a mechanism for rotating the fibers of the skirt in the same direction of the struts, allowing the skirt to elongate along the length of the struts. This allows for greater elongation of the skirt and avoids undesirable deformation of the struts when the prosthetic valve is crimped.

In addition, the spacing between the woven fibers or yarns can be increased to facilitate elongation of the skirt in the axial direction. For example, for a PET inner skirt 16 formed from 20-denier yarn, the yarn density can be about 15% to about 30% lower than in a typical PET skirt. In some examples, the yarn spacing of the inner skirt 16 can be from about 60 yarns per cm (about 155 yarns per inch) to about 70 yarns per cm (about 180 yarns per inch), such as about 63 yarns per cm (about 160 yarns per inch), whereas in a typical PET skirt the yarn spacing can be from about 85 yarns per cm (about 217 yarns per inch) to about 97 yarns per cm (about 247 yarns per inch). The oblique edges 86, 88 promote a uniform and even distribution of the fabric material along inner circumference of the frame during crimping so as to facilitate uniform crimping to the smallest possible diameter. Additionally, cutting diagonal sutures in a vertical manner may leave loose fringes along the cut edges. The oblique edges 86, 88 help minimize this from occurring.

In alternative embodiments, the skirt can be formed from woven elastic fibers that can stretch in the axial direction during crimping of the prosthetic valve. The warp and weft fibers can run perpendicularly and parallel to the upper and lower edges of the skirt, or alternatively, they can extend at angles between 0 and 90 degrees relative to the upper and lower edges of the skirt, as described above.

The inner skirt 16 can be sutured to the frame 12 at locations away from the suture line 154 so that the skirt can be more pliable in that area. This configuration can avoid stress concentrations at the suture line 154, which attaches the lower edges of the leaflets to the inner skirt 16.

As noted above, the leaflet structure 14 in the illustrated embodiment includes three flexible leaflets 41 (although a greater or a smaller number of leaflets can be used). Additional information regarding the leaflets, as well as additional information regarding skirt material, can be found, for example, in U.S. patent application Ser. No. 14/704,861, filed May 5, 2015, which is incorporated by reference in its entirety.

The leaflets 41 can be secured to one another at their adjacent sides to form commissures 122 of the leaflet structure. A plurality of flexible connectors 124 (one of which is shown in FIG. 17) can be used to interconnect pairs of adjacent sides of the leaflets and to connect the leaflets to the commissure window frame portions 30 (FIG. 5).

Figure 17:
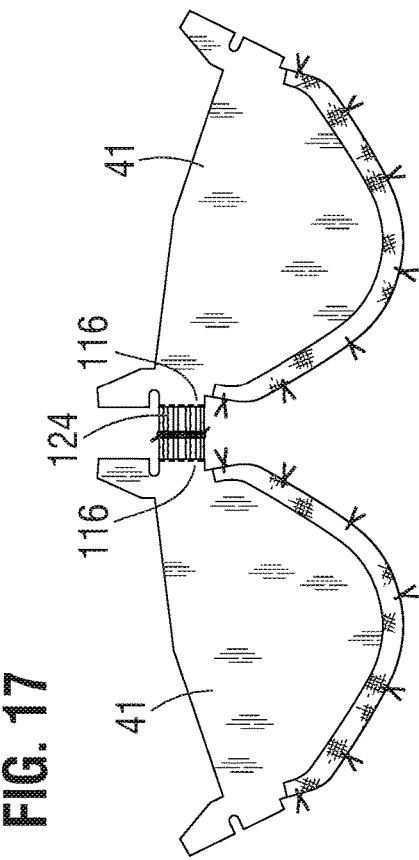
FIGS. 17-18 show the assembly of an exemplary leaflet structure.
Figure 18:
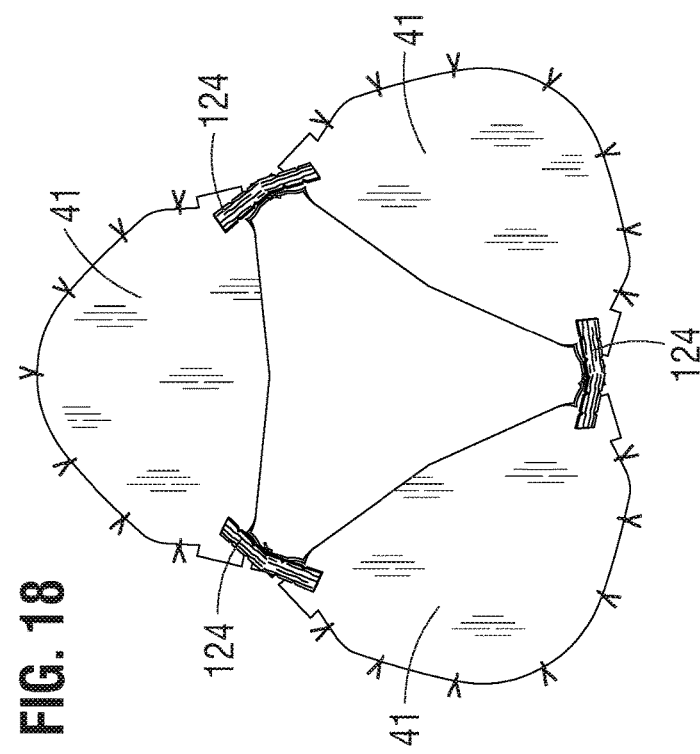

FIG. 17 shows the adjacent sides of two leaflets 41 interconnected by a flexible connector 124. Three leaflets 41 can be secured to each other side-to-side using three flexible connectors 124, as shown in FIG. 18. Additional information regarding connecting the leaflets to each other, as well as connecting the leaflets to the frame, can be found, for example, in U.S. Patent Application Publication No. 2012/0123529, which is incorporated by reference herein in its entirety.

As noted above, the inner skirt 16 can be used to assist in suturing the leaflet structure 14 to the frame. The inner skirt 16 can have an undulating temporary marking suture to guide the attachment of the lower edges of each leaflet 41. The inner skirt 16 itself can be sutured to the struts of the frame 12 using sutures 70, as noted above, before securing the leaflet structure 14 to the skirt 16. The struts that intersect the marking suture desirably are not attached to the inner skirt 16. This allows the inner skirt 16 to be more pliable in the areas not secured to the frame and minimizes stress concentrations along the suture line that secures the lower edges of the leaflets to the skirt. As noted above, when the skirt is secured to the frame, the fibers 78, 80 of the skirt (see FIG. 12) generally align with the angled struts of the frame to promote uniform crimping and expansion of the frame.

Figure 19:
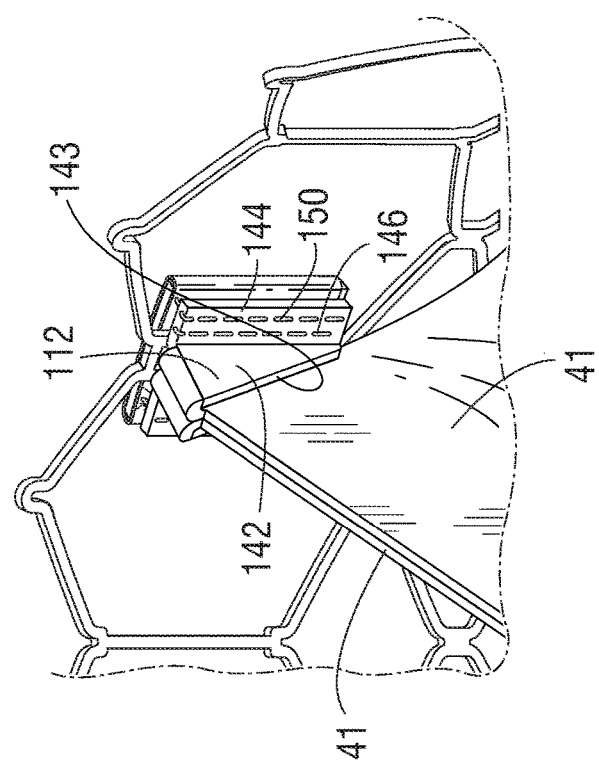
FIG. 19 shows the assembly of commissure portions of the leaflet structure with window frame portions of the frame.

FIG. 19 shows one specific approach for securing the commissure portions 122 of the leaflet structure 14 to the commissure window frame portions 30 of the frame. In this approach, the flexible connector 124 (FIG. 18) securing two adjacent sides of two leaflets is folded widthwise and the upper tab portions 112 are folded downwardly against the flexible connector. Each upper tab portion 112 is creased lengthwise (vertically) to assume an L-shape having a first portion 142 folded against a surface of the leaflet and a second portion 144 folded against the connector 124. The second portion 144 can then be sutured to the connector 124 along a suture line 146. Next, the commissure tab assembly is inserted through the commissure window 20 of a corresponding window frame portion 30, and the folds outside of the window frame portion 30 can be sutured to portions 144.

FIG. 19 also shows that the folded down upper tab portions 112 can form a double layer of leaflet material at the commissures. The inner portions 142 of the upper tab portions 112 are positioned flat against layers of the two leaflets 41 forming the commissures, such that each commissure comprises four layers of leaflet material just inside of the window frames 30. This four-layered portion of the commissures can be more resistant to bending, or articulating, than the portion of the leaflets 41 just radially inward from the relatively more-rigid four-layered portion. This causes the leaflets 41 to articulate primarily at inner edges 143 of the folded-down inner portions 142 in response to blood flowing through the prosthetic valve during operation within the body, as opposed to articulating about or proximal to the axial struts of the window frames 30. Because the leaflets articulate at a location spaced radially inwardly from the window frames 30, the leaflets can avoid contact with and damage from the frame. However, under high forces, the four layered portion of the commissures can splay apart about a longitudinal axis adjacent to the window frame 30, with each first portion 142 folding out against the respective second portion 144. For example, this can occur when the prosthetic valve 10 is compressed and mounted onto a delivery shaft, allowing for a smaller crimped diameter. The four-layered portion of the commissures can also splay apart about the longitudinal axis when the balloon catheter is inflated during expansion of the prosthetic valve, which can relieve some of the pressure on the commissures caused by the balloon, reducing potential damage to the commissures during expansion.

After all three commissure tab assemblies are secured to respective window frame portions 30, the lower edges of the leaflets 41 between the commissure tab assemblies can be sutured to the inner skirt 16. For example, as shown in FIG. 20, each leaflet 41 can be sutured to the inner skirt 16 along suture line 154 using, for example, Ethibond Excel® PET thread. The sutures can be in-and-out sutures extending through each leaflet 41, the inner skirt 16, and each reinforcing strip 72. Each leaflet 41 and respective reinforcing strip 72 can be sewn separately to the inner skirt 16. In this manner, the lower edges of the leaflets are secured to the frame 12 via the inner skirt 16. As shown in FIG. 20, the leaflets can be further secured to the skirt with blanket sutures 156 that extend through each reinforcing strip 72, leaflet 41 and the inner skirt 16 while looping around the edges of the reinforcing strips 72 and leaflets 41. The blanket sutures 156 can be formed from PTFE suture material. FIG. 21 shows a side view of the frame 12, leaflet structure 14 and the inner skirt 16 after securing the leaflet structure 14 and the inner skirt 16 to the frame 12 and the leaflet structure 14 to the inner skirt 16.

Figure 22:
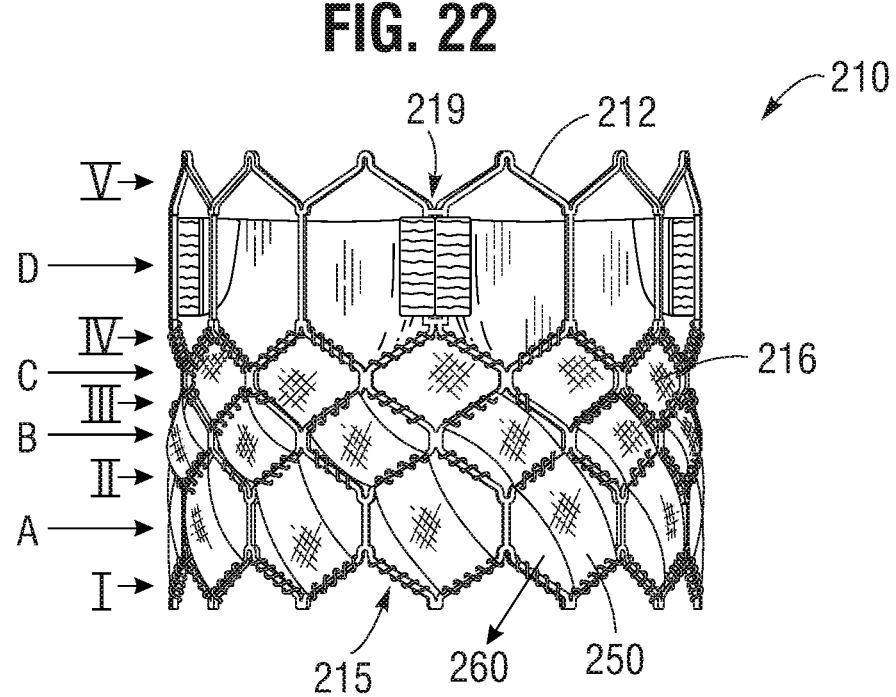
FIG. 22 shows another exemplary prosthetic heart valve.
Figure 23:
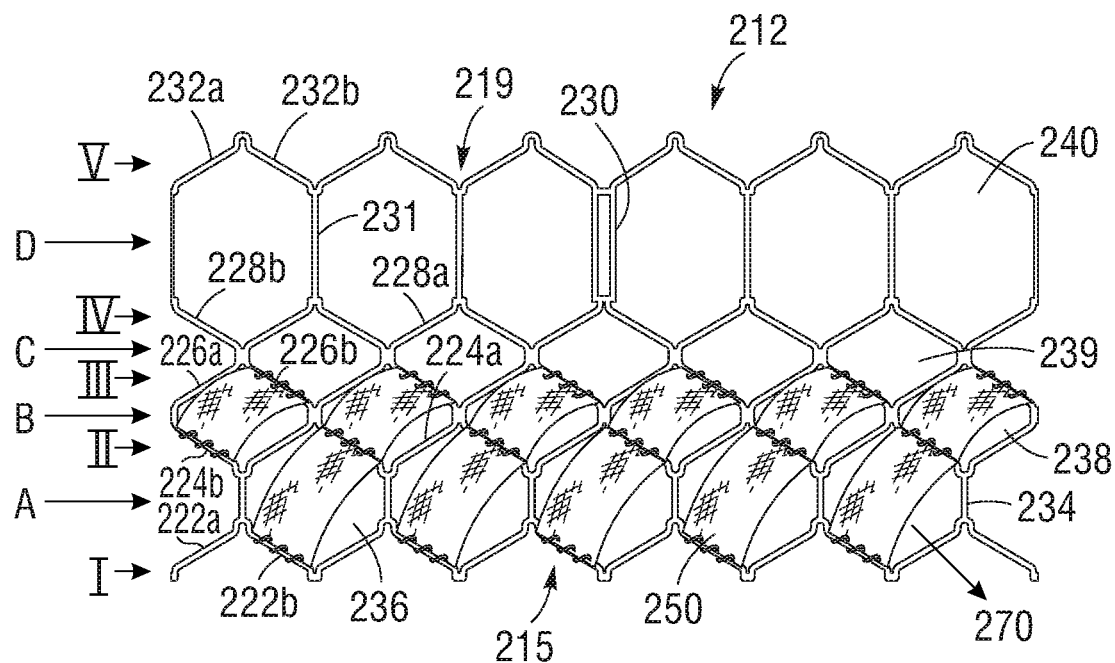
FIG. 23 shows a portion of an exemplary frame of the prosthetic heart valve of FIG. 22.

FIG. 22 shows another exemplary prosthetic heart valve 210 in an expanded configuration (e.g., when implanted in a patient). Referring to FIG. 22, the prosthetic heart valve 210 comprises a frame 212 that has a similar construction to the frame 12 of FIGS. 1-5, a valvular structure (not shown) that has a similar construction to the valvular structure 14 of FIGS. 1-3, an inner skirt 216 that has a similar construction to the inner skirt 16 of FIGS. 1-3, and sealing members 250 discussed in more detail below. FIG. 23 shows a flattened view of a portion of the frame 212 of FIG. 22 and sealing members 250.

Referring to FIGS. 22 and 23, the frame 212 has an inflow end 215 and an outflow end 219. The frame 212 in the illustrated embodiment comprises a first, lower row I of angled struts 222a and 222b arranged end-to-end and extending circumferentially at the inflow end 215 of the frame 212; a second row II of circumferentially extending, angled struts 224a and 224b; a third row III of circumferentially extending, angled struts 226a and 226b; a fourth row IV of circumferentially extending, angled struts 228a and 228b; and a fifth row V of circumferentially extending, angled struts 232a and 232b at the outflow end 219 of the frame 212. A plurality of substantially straight axially extending struts 234 can be used to interconnect the struts 222a and 222b of the first row I with the struts 224 of the second row II. The fifth row V of angled struts 232a and 232b are connected to the fourth row IV of angled struts 228a and 228b by a plurality of axially extending window frame portions 230 and a plurality of axially extending struts 231. Each axial strut 231 and each frame portion 230 extends from a location defined by the convergence of the lower ends of two angled struts 232a and 232b to another location defined by the convergence of the upper ends of two angled struts 228a and 228b. The angled struts 222a, 224a, 226a, 228a, 232a are oriented at a first angle with respect to the frame 212 and the angled struts 222b, 224b, 226b, 2228b, 232b are oriented at a second angle with respect to the frame 212.

The struts and frame portions of the frame 212 collectively define a plurality of open cells of the frame 212. At the inflow end 215 of the frame 212, struts 222, struts 224, and struts 234 define a lower row A of cells defining openings 236. The second and third rows of struts 224, 226 define a first intermediate row B of cells defining openings 238. The third and fourth rows of struts 226, 228 define a second intermediate row C of cells defining openings 239. The fourth and fifth rows of struts 228 and 232, along with frame portions 230 and struts 231, define an upper row D of cells defining openings 240.

The prosthetic heart valve 210 further comprises a plurality of sealing members 250 secured to the frame 212. The sealing members 250 can be laser cut or otherwise formed from a strong, durable material such as PET, PTFE, ePTFE, polyurethane, polyester, a fabric material, or various other suitable synthetic or natural materials configured to restrict and/or prevent blood-flow therethrough and which has a textured surface or otherwise provides a high micro-surface area. The sealing members 250 can be formed in a square or rectangular shape. Alternatively, the sealing members 250 can be formed in any geometric shape. Some of the plurality of sealing members 250 can have a different shape than other sealing members 250.

The sealing members 250 can be secured to the frame 212 within the openings of individual cells of the frame 212. The sealing members 250 can be secured to the frame 212 in a tiled pattern, wherein sealing members 250 are secured to the frame 212 in the openings of multiple cells around the frame 212. In the illustrated example of FIGS. 22 and 23, the sealing members 250 are secured to the frame 212 in openings 236 and openings 238 in rows A and B of cells. In other examples, the sealing members 250 can be secured to the frame 212 in openings 239 or openings 240 in rows C or D of cells or any combination of openings 236, 238, 239, and/or 240. In the illustrated example of FIGS. 22 and 23, the sealing members 250 are secured to the frame 212 in every opening 236 in the row A of cells and every opening 238 in row B of cells. Alternatively, the sealing members 250 can be secured to the frame 212 in some but not all of the openings 236, 238, 239, and/or 240 in rows A, B, C, and D of cells, respectively.

The sealing members 250 can be secured to the frame 212 such that two opposite sides of a sealing members 250 are secured to the frame 212 and the other two opposite sides of the sealing member 250 are not secured to the frame 212. The two opposite sides of the sealing members 250 that are secured to the frame 212 can each be secured to a different strut of the frame 212. In the illustrated example of FIGS. 22 and 23, the sealing members 250 in the row A of cells are secured to struts 222 and 224. The sealing members 250 in row B of cells are secured to struts 224 and 226. Alternatively, or in addition, the sealing members 250 can be secured to struts 228 and/or struts 232. In other examples, the sealing members 250 can be secured to axially straight struts 234 and/or axial struts 231. In the illustrated example, each sealing member 250 is secured to the frame 212 within an opening of one cell. Alternatively, sealing members can span multiple cells. For example, one side of a sealing member can be secured to an angled strut 226 and the opposite side of the sealing member can be secured to an angled strut 222 such that the sealing member spans two adjacent cells, one cell in row A and one cell in row B. Moreover, the sealing members 250 can be formed from individual pieces of material sized to cover a single cell, or from one or more pieces of material sized so as to be attached to multiple cells. In the illustrated example, the sealing members 250 are secured to the frame 212 with sutures. Alternatively, the sealing members 250 can be secured to the frame 212 with adhesive, ultrasonic welding or other means in addition to or in lieu of sutures.

In the illustrated example of FIGS. 22 and 23, the length of each of the sealing members 250 is greater than the distance between the struts that the sealing members 250 are secured to. That is, the sealing members 250 are not tautly secured to the frame 212 but rather there is excess material in each of the cells of the frame 212 that contains a sealing member 250. Thus, when the prosthetic heart valve 210 is implanted in a valve of a patient, the openings form channels or pathways where any antegrade blood flow along the outside of the frame 212 is exposed to more material surface area, causing the flow of blood to slow down and induces clotting. The excess material of the sealing members 250 may also expand away from the frame 212 to help seal any gaps between the prosthetic heart valve 210 and the native anatomy.

The sealing members 250 can be secured to the frame 212 in one of two orientations, a clockwise orientation or a counter-clockwise orientation, as defined herein. In the illustrated example of FIG. 22, each of the sealing members 250 are secured to the frame 212 in a clockwise orientation. In the illustrated example of FIG. 24, each of the sealing members 250 are secured to the frame 212 in a counter-clockwise orientation. In the clockwise orientation as shown in the example of FIG. 22, the sealing members 250 in row A of cells are secured to the frame 212 at struts 222*a* and 224*a* and the sealing members 250 in row B of cells are secured to the frame 212 at struts 224*a* and 226*a*. This creates a diagonal path in a direction 260 along the outside of the frame 212 along which antegrade blood will be forced to travel by the sealing members 250. As antegrade blood flows between the frame 212 and the sealing members 250 in direction 260, this blood travels in a clockwise direction around the frame 212 with respect to a circular cross-section through the frame 212.

In the counter-clockwise orientation as shown in FIG. 23, each of the sealing members 250 in row A of cells are secured to the frame 212 at struts 222*b* and 224*b* and each of the sealing members 250 in row B of cells are secured to the frame 212 at struts 224*b* and 226*b*. This creates a diagonal path in a direction 270 along the outside of the frame 212 along which antegrade blood will be forced to travel by the sealing members 250. As antegrade blood flows between the frame 212 and the sealing members 250 in direction 270, this blood travels in a counter-clockwise direction around the frame 212 with respect to a circular cross-section through the frame 212. As noted above, by forcing antegrade blood to flow along a path in a diagonal direction with respect to the frame 212, the blood is exposed to more of the surface area of the sealing members 250 which can slow the flow of this antegrade blood and inducing clotting that can help seal any gaps between the prosthetic heart valve 210 and the native anatomy. The plurality of sealing members 250 therefore cooperate with the inner skirt 216 to avoid perivalvular leakage after implantation of the prosthetic valve 210. In several embodiments, the prosthetic valve 210 can have reduced perivalvular leakage when implanted in a subject compared to a similar prosthetic valve that lacks the plurality of sealing members 250.

Figure 24:
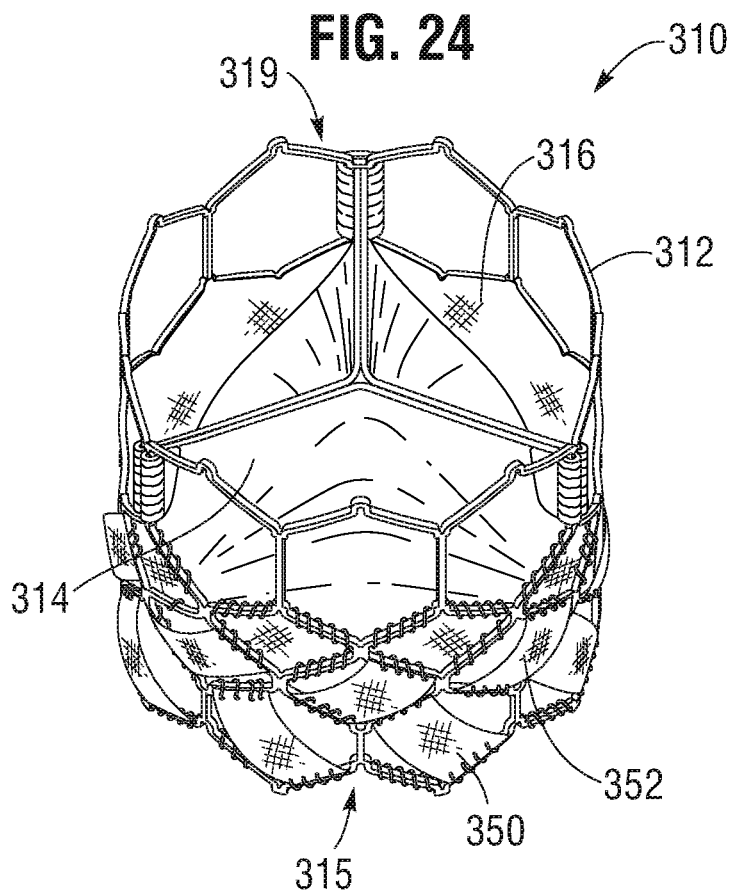
FIG. 24 shows another exemplary prosthetic heart valve.
Figure 25:
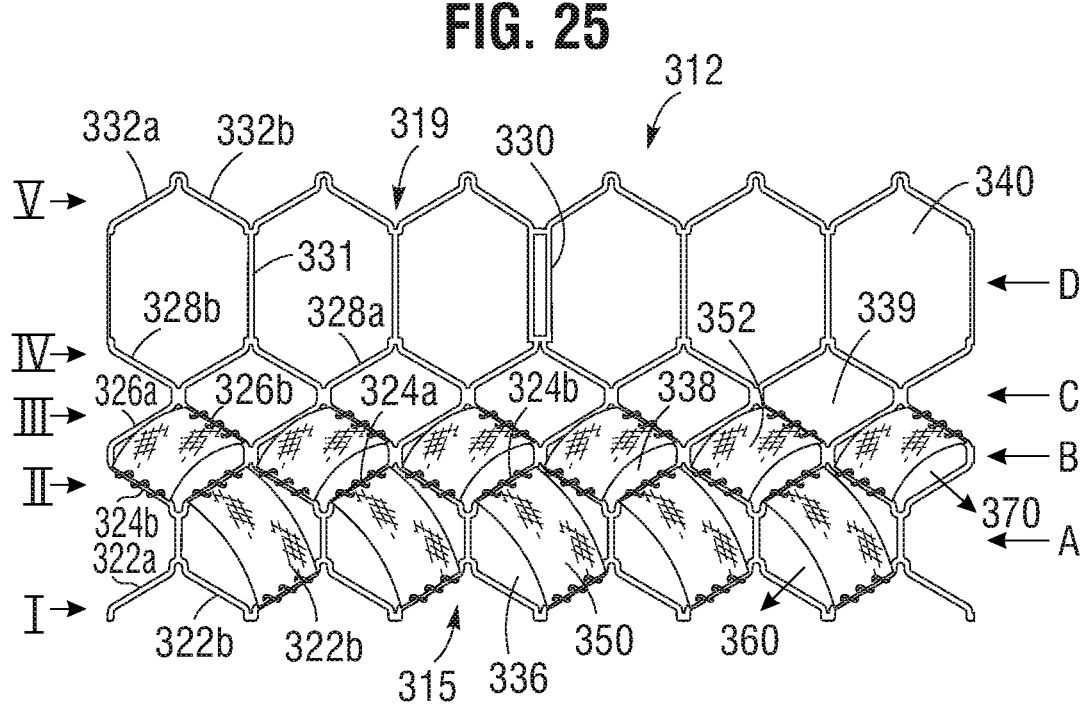
FIG. 25 shows a portion of an exemplary frame of the prosthetic heart valve of FIG. 24.

FIG. 24 shows another exemplary prosthetic heart valve 310 in an expanded configuration (e.g., when implanted in a patient). Referring to FIG. 24, the prosthetic heart valve 310 comprises a frame 312 that has a similar construction to the frame 212 of FIGS. 1-5, a valvular structure 314 that has a similar construction to the valvular structure 14 of FIGS. 1-3, an inner skirt 316 that has a similar construction to the inner skirt 16 of FIGS. 1-3, and sealing members 350 and 352 that have a similar construction to the sealing members 250 of FIGS. 22-23. FIG. 25 shows a flattened view of a portion of the frame 312 of FIG. 24 and sealing members 350, 352.

The elements of the prosthetic heart valve 310 are identical to the elements of prosthetic heart valve 210 except that the sealing members 350 are secured to the frame 312 with different orientations than the sealing members 352, whereas all of sealing members 250 are secured to the frame 210 with the same orientation. Referring to FIGS. 24 and 25, the frame 312 has an inflow end 315 and an outflow end 319. The frame 312 in the illustrated embodiment comprises a first, lower row I of angled struts 322*a* and 322*b* arranged end-to-end and extending circumferentially at the inflow end 315 of the frame 312; a second row II of circumferentially extending, angled struts 324*a* and 324*b*; a third row III of circumferentially extending, angled struts 326*a* and 326*b*; a fourth row IV of circumferentially extending, angled struts 328*a* and 328*b*; and a fifth row V of circumferentially extending, angled struts 332*a* and 332*b* at the outflow end 319 of the frame 312. A plurality of substantially straight axially extending struts 334 can be used to interconnect the struts 322*a* and 322*b* of the first row I with the struts 324 of the second row II. The fifth row V of angled struts 332*a* and 332*b* are connected to the fourth row IV of angled struts 328*a* and 328*b* by a plurality of axially extending window frame portions 330 and a plurality of axially extending struts 331. Each axial strut 331 and each frame portion 330 extends from a location defined by the convergence of the lower ends of two angled struts 332*a* and 332*b* to another location defined by the convergence of the upper ends of two angled struts 328*a* and 328*b*. The angled struts 322*a*, 324*a*, 326*a*, 328*a*, 332*a* are oriented at a first angle with respect to the frame 312 and the angled struts 322*b*, 324*b*, 326*b*, 3228*b*, 332*b* are oriented at a second angle with respect to the frame 312.

The struts and frame portions of the frame 312 collectively define a plurality of open cells of the frame 312. At the inflow end 315 of the frame 312, struts 322, struts 324, and struts 334 define a lower row A of cells defining openings 336. The second and third rows of struts 324, 326 define a first intermediate row B of cells defining openings 338. The third and fourth rows of struts 326, 328 define a second intermediate row C of cells defining openings 339. The fourth and fifth rows of struts 328 and 332, along with frame portions 330 and struts 331, define an upper row D of cells defining openings 340.

The sealing members 350, 352 are similar in construction to the sealing members 250 of FIGS. 22-23 and they can be secured to the frame 312 in a similar manner as the sealing members 250 are secured to the frame 212. In the illustrated example of FIGS. 24 and 25, the sealing members 350 are secured to the frame 312 in openings 336 in row A of cells and the sealing members 352 are secured to the frame 312 in row B of cells. In other examples, sealing member can be secured to the frame 312 in openings 339 or openings 340 in rows C or D of cells or any combination of openings 336, 338, 339, and/or 340. In the illustrated example of FIGS. 24 and 25, the sealing members 350 are secured to the frame 312 in every opening 336 in the row A of cells and the sealing members 352 are secured to the frame 312 in every opening 338 in row B of cells. Alternatively, the sealing members 350, 352 can be secured to the frame 312 in some but not all of the openings 336, 338, 339, and/or 340 in rows A, B, C, and/or D of cells, respectively.

In the illustrated example of FIGS. 24-25, the sealing members 350 in row A of cells are secured to the frame 312 in a clockwise orientation and the sealing members 352 in row B of cells are secured to the frame 312 in a counter-clockwise orientation as described above in connection with FIGS. 22-23. That is, the sealing members 350 in row A of cells are secured to the frame 312 at struts 322*a* and 324*a*, creating a path in a direction 360 through which antegrade blood can flow between the frame 312 and the sealing members 350 in the openings 336 in row A of cells. The sealing members 352 in row B of cells are secured to the frame 312 at struts 324*b* and 326*b*. This creates a path in a direction 370 through which antegrade blood can flow between the frame 312 and the sealing members 352 in the openings 338 of row B of cells. Because the sealing members 350 in row A of cells are secured to the frame 312 with a different orientation than the sealing members 352 in row B of cells, antegrade blood flow between the frame 312 and the sealing members 350, 352 must travel a more circuitous route than in the example of FIGS. 22-23, which can further slow this antegrade blood flow and can further increase blood clotting which can help seal any gaps between the prosthetic heart valve 310 and the native anatomy when the prosthetic heart valve 310 is implanted in a patient. The plurality of sealing members 350, 352 therefore cooperate with the inner skirt 316 to avoid perivalvular leakage after implantation of the prosthetic valve 310. In several embodiments, the prosthetic valve 310 can have reduced perivalvular leakage when implanted in a subject compared to a similar prosthetic valve that lacks the plurality of sealing members 350, 352. In other examples, the sealing members 350, 352 can be secured to the frame 312 in either a clockwise or counter-clockwise orientation.

The prosthetic valve 210 or 310 can be configured for and mounted on a suitable delivery apparatus for implantation in a subject. Several catheter-based delivery apparatuses can be used; a non-limiting example of a suitable catheter-based delivery apparatus includes that disclosed in U.S. Patent Application Publication No. 2013/0030519, which is incorporated by reference herein in its entirety, and U.S. Patent Application Publication No. 2012/0123529.

To implant a plastically-expandable prosthetic valve 210 or 310 within a patient, the prosthetic valve 210, 310 can be crimped on an elongated shaft 180 of a delivery apparatus, as best shown in FIG. 13. The prosthetic valve, together with the delivery apparatus, can form a delivery assembly for implanting the prosthetic valve 210, 310 in a patient's body. The shaft 180 comprises an inflatable balloon 182 for expanding the prosthetic valve within the body. With the balloon 182 deflated, the prosthetic valve 210, 310 can then be percutaneously delivered to a desired implantation location (e.g., a native aortic valve region). Once the prosthetic valve 210, 310 is delivered to the implantation site (e.g., the native aortic valve) inside the body, the prosthetic valve 210, 310 can be radially expanded to its functional state by inflating the balloon 182.

Alternatively, a self-expanding prosthetic valve 210, 310 can be crimped to a radially collapsed configuration and restrained in the collapsed configuration by inserting the prosthetic valve 210, 310 into a sheath or equivalent mechanism of a delivery catheter. The prosthetic valve 210, 310 can then be percutaneously delivered to a desired implantation location. Once inside the body, the prosthetic valve 210, 310 can be advanced from the delivery sheath, which allows the prosthetic valve to expand to its functional state.

Figure 26:
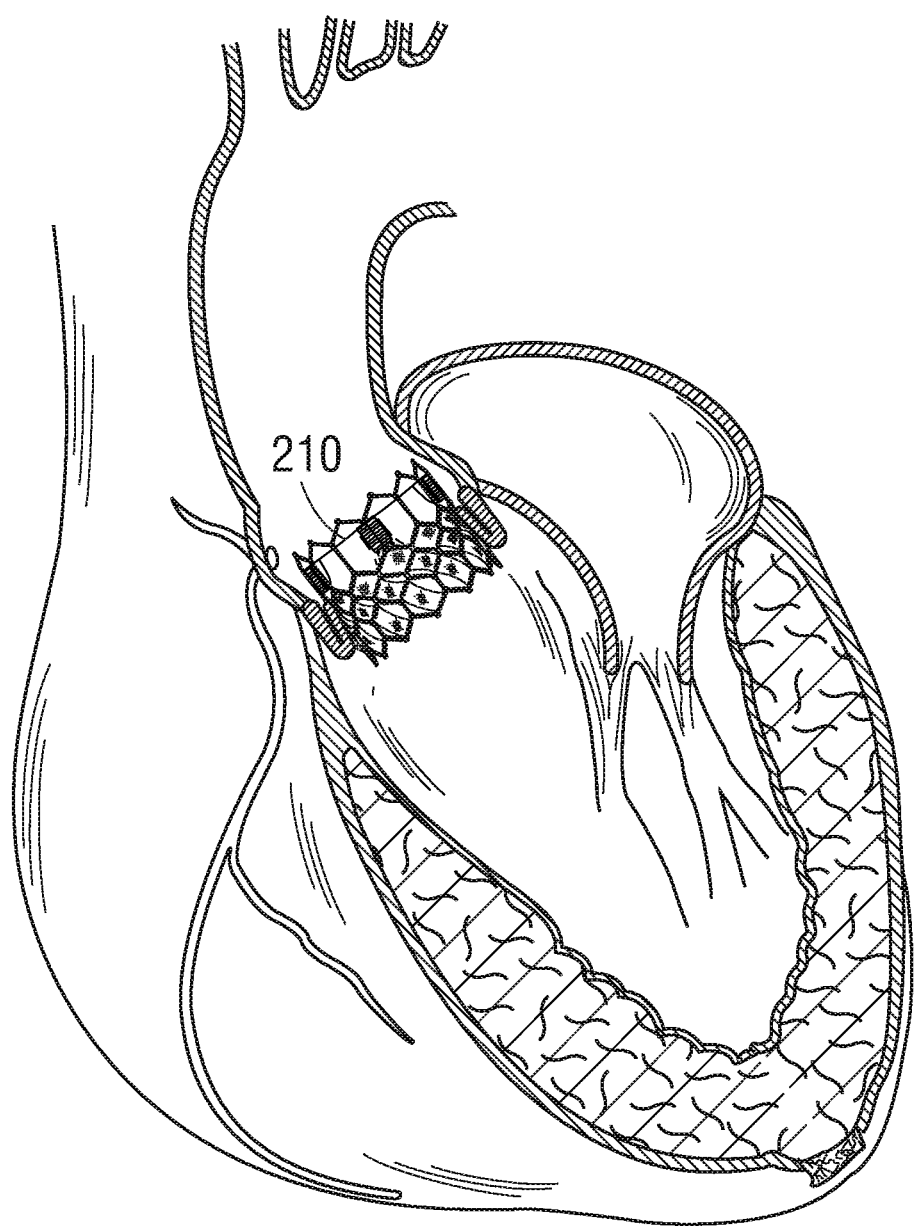
FIG. 26 shows an exemplary prosthetic heart valve implanted in the native aortic valve of a patient.

FIGS. 26-28 and 31 show various implantation positions for a prosthetic heart valve 210 or 310, including implantation within a dock or anchor placed inside the patient's body prior to valve implantation. For purposes of illustration, FIGS. 26-28 each show an implantation of prosthetic heart valve 210. However, it should be understood that in each of FIGS. 26-28, the prosthetic heart valve 210 can be replaced with the prosthetic heart valve 310. FIG. 26 shows the prosthetic heart valve 210 implanted in the native aortic valve of a patient.

Figure 27:
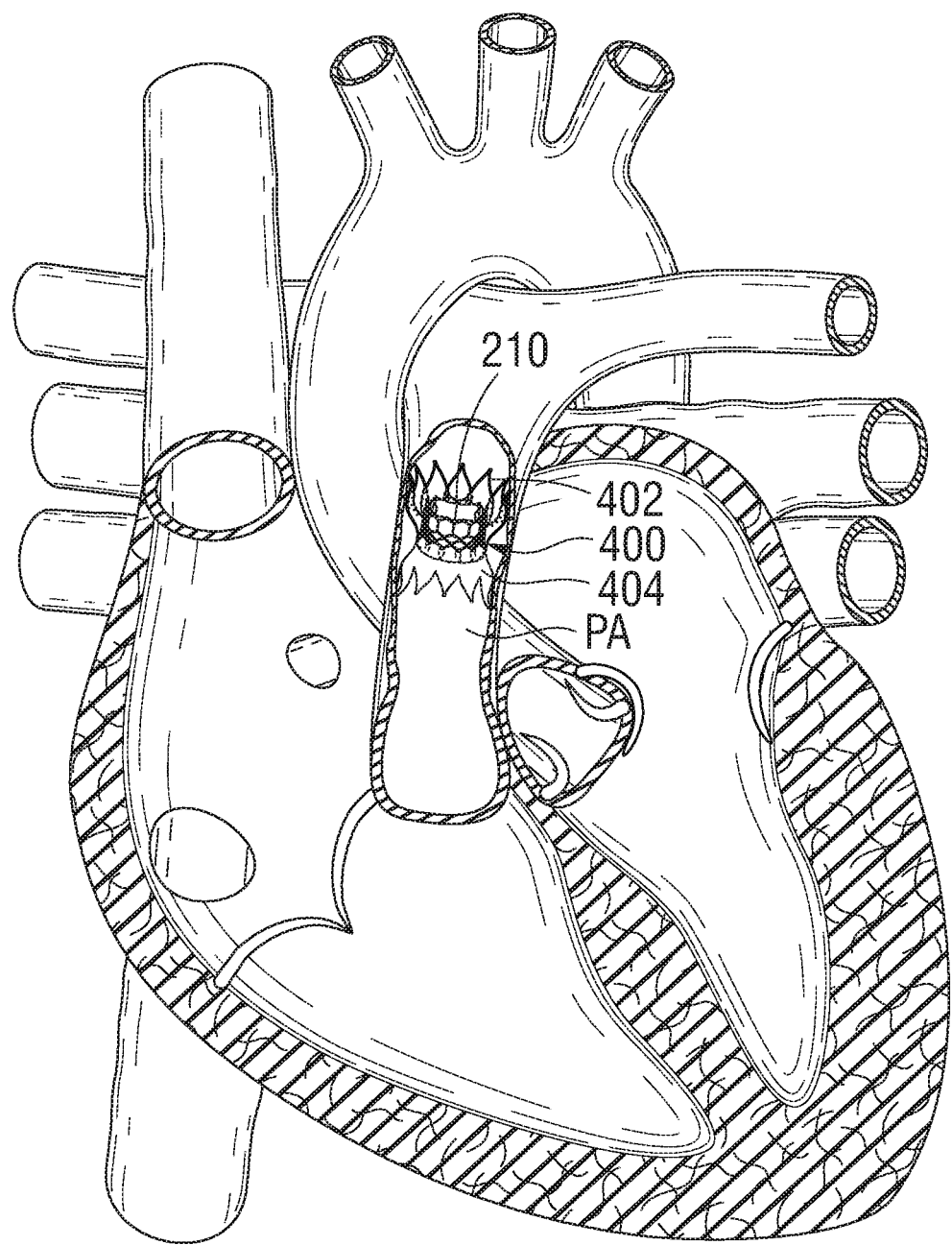
FIG. 27 shows an exemplary prosthetic heart valve and docking device implanted in the pulmonary artery of a patient.

FIG. 27 shows the prosthetic heart valve 210 implanted in the pulmonary artery of a patient for replacing or enhancing the function of a diseased pulmonary valve. Due to the variations in the size and shape of the native pulmonary valve and the pulmonary artery, the prosthetic valve 210 can be implanted within a radially expandable outer docking device 400. The docking device 400 can comprise a radially expandable and compressible annular stent 402 and a sealing member 404 that covers all or a portion of the stent and can extend across the inner surface and/or outer surface of the stent. The docking device 400 is configured to engage the inner wall of the pulmonary artery and can accommodate variations in patient anatomy. The docking device 400 also can compensate for the expanded prosthetic heart valve 410 being much smaller than vessel in which it is placed. The docking device 400 also can be used to support a prosthetic valve in other areas of the patient's anatomy, such as, the inferior vena cava, superior vena cava, or the aorta. Further details of the docking device 400 and methods for implanting the docking device and a prosthetic valve are disclosed, for example, in co-pending U.S. application Ser. No. 15/422,354, filed Feb. 1, 2017, which is incorporated herein by reference in its entirety.

Figure 28:
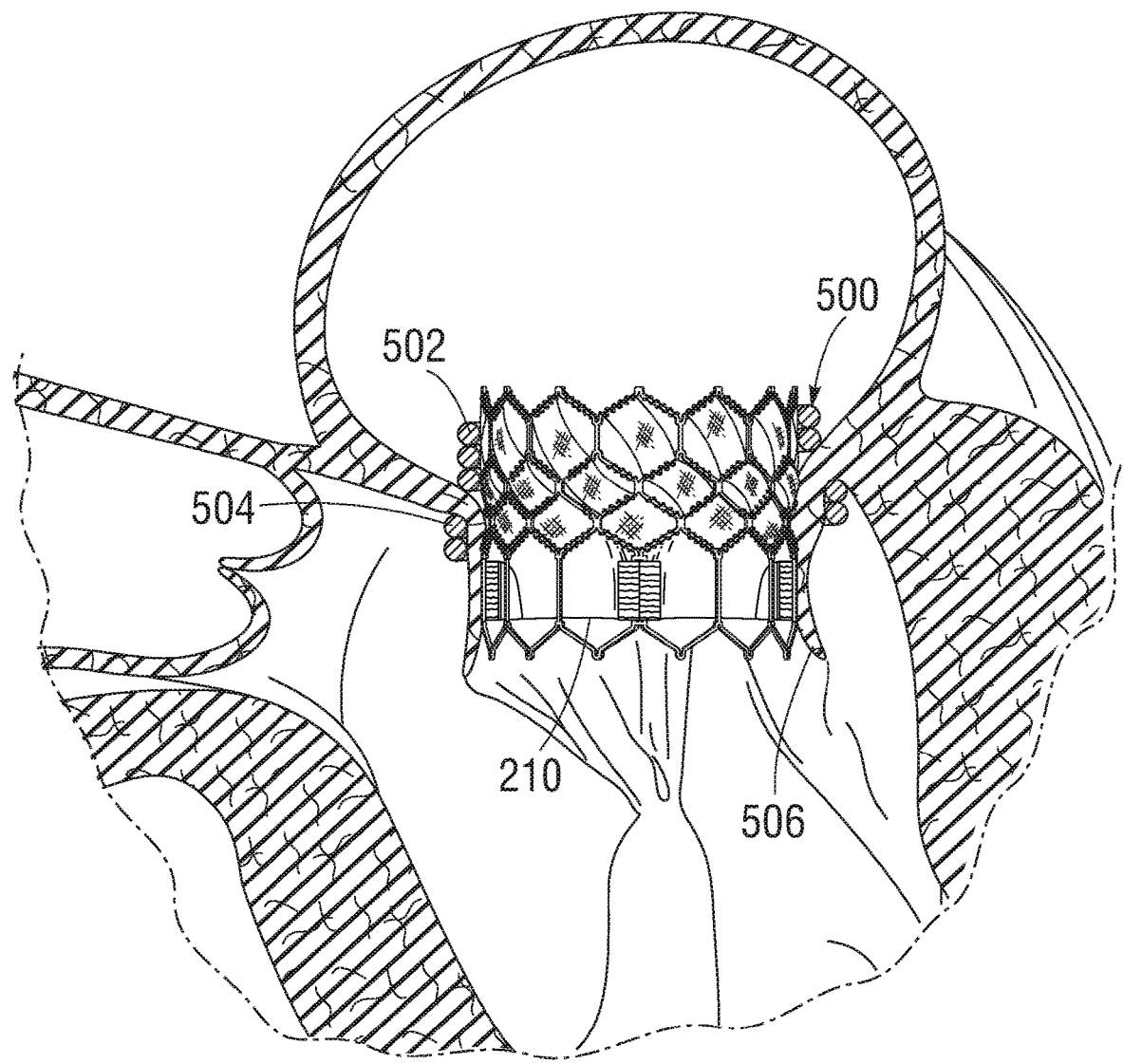
FIG. 28 shows an exemplary prosthetic heart valve and docking device implanted in the native mitral valve of a patient.

FIG. 28 shows the prosthetic heart valve 210 implanted in the native mitral valve of a patient using a docking device in the form of a helical anchor 500. The helical anchor 500 can include one or more coils 502 deployed in left atrium and one or more coils 504 deployed in the left ventricle and radially outside of the native mitral valve leaflets 506. When the prosthetic valve 210 is deployed within the native valve, the native leaflets are compressed or pinched between the prosthetic valve 210 and the anchor 500 to retain the prosthetic valve in place. Further details of the helical anchor 500 and methods for implanting the anchor and a prosthetic valve are disclosed, for example, in U.S. Application No. 62/395,940, filed Sep. 16, 2016, which is incorporated herein by reference in its entirety.

FIGS. 29 and 30 show a docking device 600 for a prosthetic heart valve, according to another embodiment. The docking device 600 can include a radially expandable and compressible frame 602 having an outer portion 604, an inner portion 606 disposed coaxially within one end portion of the outer portion 604, and a curved transition portion 608 extending between and connecting the inner portion 606 and the outer portion 604. The docking device 600 can further include a sealing member 610 extending over the inner surface of the inner portion 606, a portion of the outer surface of the outer portion 604 adjacent the inner portion 606, and the transition portion 608.

Figure 31:
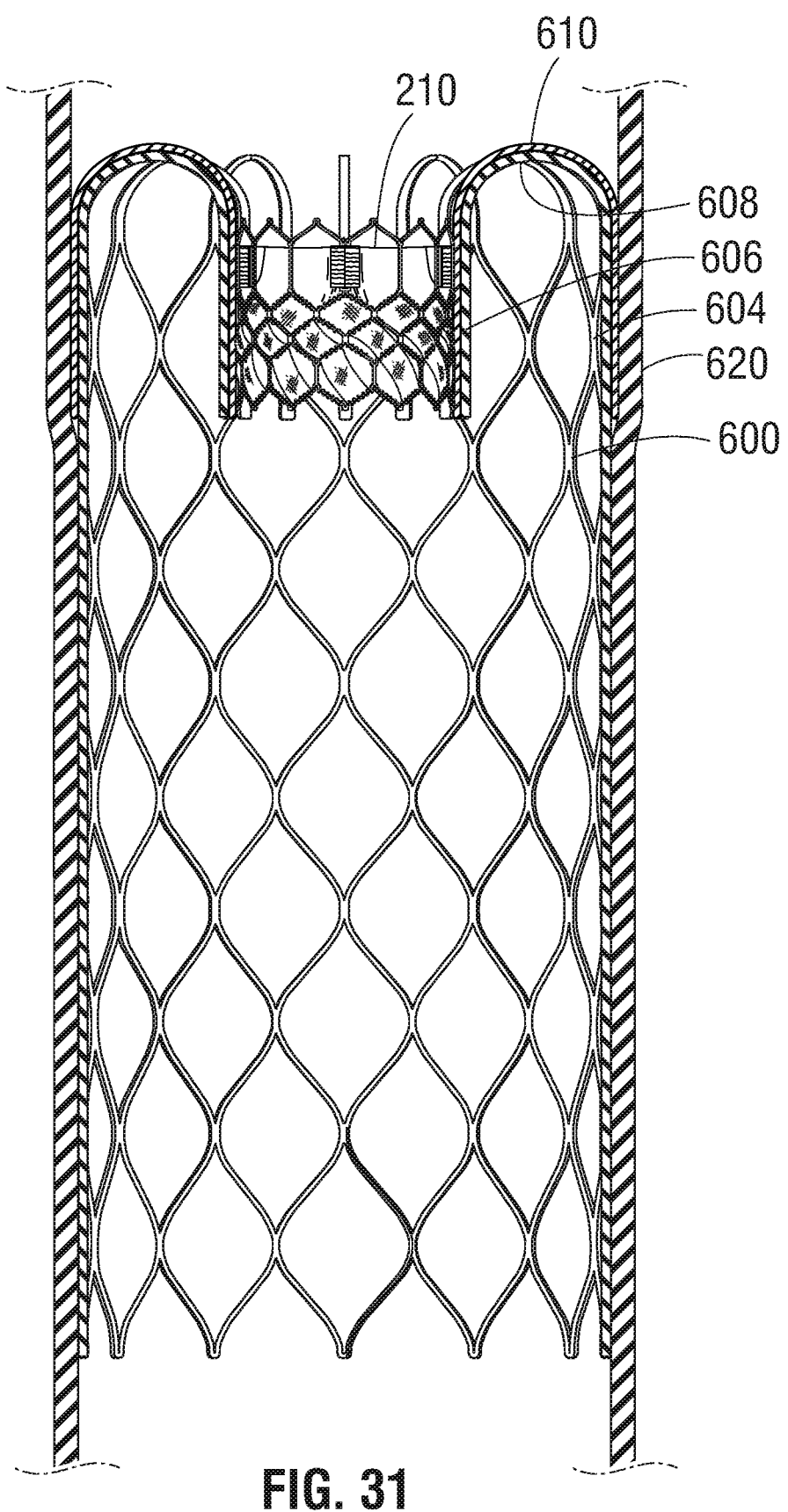
FIG. 31 shows an exemplary prosthetic heart valve and the docking device of FIGS. 29-30 implanted in the inferior vena cava of a patient.

FIG. 31 shows the docking device 600 implanted in a vessel 620, which can be, for example, the inferior vena cava, superior vena cava, or the ascending aorta. As shown, a prosthetic valve 210 can be deployed within the inner portion 606 of the docking device 600. Similar to the docking device 400, the docking device 600 can compensate for the expanded prosthetic heart valve 210 being much smaller than vessel in which it is placed. The docking device 600 is particularly suited for implanting a prosthetic valve in the inferior vena cava for replacing or enhancing the function of the native tricuspid valve. Further details of the docking device 600 and methods for implanting the docking device and a prosthetic valve are disclosed, for example, in co-pending U.S. application Ser. No. 16/034,794, filed Jul. 13, 2018, which is incorporated herein by reference.

General Considerations

It should be understood that the disclosed valves can be implanted in any of the native annuluses of the heart (e.g., the pulmonary, mitral, and tricuspid annuluses), and can be used with any of various approaches (e.g., retrograde, antegrade, transseptal, transventricular, transatrial, etc.). The disclosed prostheses can also be implanted in other lumens of the body.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

As used in this application and in the claims, the singular forms "a," "an," and "the" include the plural forms unless the context clearly dictates otherwise. Additionally, the term "includes" means "comprises."

As used herein, the term "and/or" used between the last two of a list of elements means any one or more of the listed elements. For example, the phrase "A, B, and/or C" means "A", "B", "C", "A and B", "A and C", "B and C", or "A, B, and C".

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "coupled" and "associated" generally mean physically coupled or linked and does not exclude the presence of intermediate elements between the coupled or associated items absent specific contrary language.

As used herein, operations that occur "simultaneously" or "concurrently" occur generally at the same time as one another, although delays in the occurrence of one operation relative to the other due to, for example, spacing, play or backlash between components in a mechanical linkage such as threads, gears, etc., are expressly within the scope of the above terms, absent specific contrary language.

In view of the many possible embodiments to which the principles disclosed herein may be applied, it should be recognized that the illustrated embodiments are only preferred examples and should not be taken as limiting the scope of the disclosure. Rather, the scope of the disclosure is at least as broad as the following claims.

The invention claimed is:

1. An implantable prosthetic valve comprising:
   an annular frame comprising an inflow end, an outflow end, and a plurality of struts forming a plurality of cells, wherein each of the cells defines an opening in the frame, and wherein the frame is radially collapsible and expandable between a radially collapsed configuration and a radially expanded configuration;
   a leaflet structure positioned within the frame and secured thereto; and
   a plurality of sealing members positioned within the openings of a plurality of the cells of the frame and secured thereto, wherein each of the sealing members is positioned within a respective one of the openings, and wherein each of the sealing members includes two opposite sides that are not secured to the frame to allow blood to flow through each of the sealing members along a path formed between the frame and the sealing members.

2. The prosthetic valve of claim 1, wherein the frame comprises multiple rows of cells and wherein one of the sealing members is secured within each cell of the row of cells closest to the inflow end of the frame.

3. The prosthetic valve of claim 1, wherein the frame comprises multiple rows of cells and wherein one of the sealing members is secured within each cell of the two rows of cells closest to the inflow end of the frame.

4. The prosthetic valve of claim 3, wherein the sealing members in one of the two rows of cells closest to the inflow end of the frame each have a first orientation with respect to the frame and the sealing members in the other of the first two rows of cells closest to the inflow end of the frame each have a second orientation different from the first orientation.

5. The prosthetic valve of claim 1, wherein each of the sealing members has the same orientation within the respective one of the openings, with respect to the frame, wherein the orientation is a diagonal orientation where each sealing member extends diagonally across the respective one of the openings in which it is positioned.

6. The prosthetic valve of claim 1, wherein a first set of the sealing members each have a first orientation within the respective one of the openings, with respect to the frame, and the remainder of the sealing members not in the first set each have a second orientation within the respective one of the openings, with respect to the frame, that is different from the first orientation, wherein the first orientation and the second orientation are diagonal orientations where each sealing member is secured to each of and extends between two angled struts forming the respective one of the openings, the two angled struts being part of a different row of angled struts of the frame and angled in a same direction.

7. The prosthetic valve of claim 1, wherein the sealing members are secured to the frame with sutures.

8. The prosthetic valve of claim 1, further comprising an inner skirt arranged around an inner surface of the frame and secured thereto.

9. The prosthetic valve of claim 1, wherein the sealing members are loosely secured to the frame such that the sealing members positioned within the cells of the frame comprise excess material to expand away from the frame when blood flows along an outer surface of the frame, along the path formed between the frame and the sealing members in the openings, wherein the path is a diagonal path.

10. The prosthetic valve of claim 1, wherein the sealing members are positioned such that when the prosthetic valve is implanted, antegrade blood flows in a diagonal path between the frame and the plurality of sealing members, on an outside of the frame.

11. An implantable prosthetic valve, comprising:
    an annular frame comprising an inflow end, an outflow end, and a plurality of struts forming a plurality of cells, wherein each of the cells defines an opening in the frame, and wherein the frame is radially collapsible and expandable between a radially collapsed configuration and a radially expanded configuration;
    a leaflet structure positioned within the frame and secured thereto; and
    a plurality of sealing members positioned within the openings of a plurality of the cells of the frame and secured thereto, wherein each of the sealing members is positioned within a respective one of the openings, wherein the sealing members are substantially rectangular and two opposite sides of each of the sealing members are secured to the frame and the other two opposite sides of each of the sealing members are not secured to the frame.

12. The prosthetic valve of claim 11, wherein the two opposite sides of each of the sealing members are secured to the struts of the frame and the other two opposite sides of each of the sealing members are not secured to the frame.

13. An implantable prosthetic valve, comprising:
an annular frame comprising an inflow end, an outflow end, and a plurality of struts forming a plurality of cells, wherein each of the cells defines an opening in the frame, and wherein the frame is radially collapsible and expandable between a radially collapsed configuration and a radially expanded configuration;
a leaflet structure positioned within the frame and secured thereto; and
a plurality of sealing members positioned within the openings of a plurality of the cells of the frame and secured thereto, wherein each of the sealing members is positioned within a respective one of the openings, wherein a first set of the sealing members each have a first orientation within the respective one of the openings, with respect to the frame, and the remainder of the sealing members not in the first set each have a second orientation within the respective one of the openings, with respect to the frame, that is different from the first orientation, wherein the first orientation is a clockwise orientation and wherein the second orientation is a counter-clockwise orientation.

14. An implantable prosthetic valve, comprising:
an annular frame comprising an inflow end, an outflow end, and a plurality of struts forming a plurality of cells, wherein each of the cells defines an opening in the frame, and wherein the frame is radially collapsible and expandable between a radially collapsed configuration and a radially expanded configuration;
a leaflet structure positioned within the frame and secured thereto; and
a plurality of sealing members positioned within the openings of a plurality of the cells of the frame and secured thereto, wherein each of the sealing members is positioned within a respective one of the openings, wherein the frame comprises multiple rows of cells and wherein one of the sealing members is secured within each cell of the two rows of cells closest to the inflow end of the frame, wherein the sealing members in one of the two rows of cells closest to the inflow end of the frame each have a first orientation with respect to the frame and the sealing members in the other of the first two rows of cells closest to the inflow end of the frame each have a second orientation different from the first orientation, and wherein the first orientation is a clockwise orientation and the second orientation is a counter-clockwise orientation.

15. An assembly for implanting a prosthetic heart valve, comprising:
a delivery apparatus comprising an elongate shaft; and
a prosthetic heart valve, comprising:
an annular frame comprising an inflow end, an outflow end, and a plurality of struts forming a plurality of cells, wherein each of the cells defines an opening in the frame, and wherein the frame is radially collapsible and expandable between a radially collapsed configuration and a radially expanded configuration;
a leaflet structure positioned within the frame and secured thereto; and
a plurality of sealing members positioned within the openings of the plurality of the cells of the frame and secured thereto, wherein each of the sealing members is positioned within a respective one of the openings, and wherein each sealing member includes a first two opposite sides that are secured to the frame and a second two opposite sides that are not secured to the frame to allow blood to flow through each sealing member along a diagonal path formed between the frame and the sealing members;
wherein the prosthetic heart valve is coupled to the shaft of the delivery apparatus.

16. The assembly of claim 15, wherein each of the sealing members has the same orientation within the respective one of the openings, with respect to the frame.

17. The assembly of claim 16, wherein the orientation is a diagonal orientation where each sealing member extends diagonally across the respective one of the openings in which it is positioned.

18. The prosthetic valve of claim 15, wherein a first set of the sealing members each have a first orientation within the respective one of the openings, with respect to the frame, and the remainder of the sealing members not in the first set each have a second orientation within the respective one of the openings, the second orientation different than the first orientation.

19. The assembly of claim 18, wherein the first orientation and the second orientation are diagonal orientations.

20. The assembly of claim 19, wherein each sealing member is secured to each of and extends between two angled struts forming the respective one of the openings, the two angled struts being part of a different row of angled struts of the frame and angled in a same direction.

* * * * *